United States Patent

Brunengraber et al.

[19]

[11] Patent Number: 6,086,789
[45] Date of Patent: Jul. 11, 2000

[54] MEDICAL USES OF PYRUVATES

[75] Inventors: Henri Brunengraber, Shaker Heights, Ohio; Catherine Bomont, Scotch Plains, N.J.; France David, Shaker Heights, Ohio; Peter T. Hallowell, Cleveland Heights, Ohio; Kevin D. Cooper, Moreland Hills, Ohio; Takhar Kasoumov, Cleveland, Ohio

[73] Assignee: Case Western Reserve University, Cleveland, Ohio

[21] Appl. No.: 09/076,374

[22] Filed: May 12, 1998

Related U.S. Application Data

[63] Continuation-in-part of application No. 08/807,585, Feb. 27, 1997, Pat. No. 5,876,916, which is a continuation-in-part of application No. 08/617,285, Mar. 18, 1996, Pat. No. 5,667, 962

[60] Provisional application No. 60/046,343, May 13, 1997, and provisional application No. 60/080,695, Apr. 3, 1998.

[51] Int. Cl.[7] ............................... A61K 7/48; A61K 9/20; A61K 31/255; C07G 3/00; C07H 13/02

[52] U.S. Cl. .......................... 252/399; 252/407; 424/1.25; 424/401; 424/464; 514/533; 514/545; 514/547; 514/675; 514/706; 514/724; 514/738; 536/4.1; 536/115; 536/118; 536/119

[58] Field of Search ..................................... 514/738, 547, 514/706, 724, 675, 533, 545; 536/4.1, 115, 118, 119; 252/399, 407; 424/1.25, 401, 464, 465

[56] References Cited

U.S. PATENT DOCUMENTS

| | | | |
|---|---|---|---|
| 3,781,267 | 12/1973 | Jacques et al. ....................... | 260/210 R |
| 4,970,143 | 11/1990 | Guidoux et al. ............................. | 435/1 |
| 5,075,210 | 12/1991 | Wikman-Coffelt .......................... | 435/1 |
| 5,283,260 | 2/1994 | Miller et al. ............................... | 514/563 |
| 5,294,641 | 3/1994 | Stanko ...................................... | 514/540 |
| 5,480,909 | 1/1996 | Stanko ...................................... | 514/557 |
| 5,580,902 | 12/1996 | Yu et al. ................................... | 514/546 |
| 5,602,183 | 2/1997 | Martin et al. ............................. | 514/724 |
| 5,614,561 | 3/1997 | Martin ...................................... | 514/724 |
| 5,691,380 | 11/1997 | Mason et al. ............................. | 514/562 |
| 5,693,670 | 12/1997 | Philippe et al. .......................... | 514/545 |

OTHER PUBLICATIONS

Effects of Pyruvate and Dihydroxyacetone Consumption on the Growth and Metabolic State of Obese Zucker Rats[1–3]. Am J Clin Nutr 1991;53:847–53. 1991 American Society for Clinical Nutrition.

Inhibition of Lipid Accumulation and Enhancement of Energy Expenditure by the Addition of Pyruvate and Dihydroxyacetone to a Rat Diet Metabolism, vol., 35, No. 5 (Feb.), 1986: pp. 182–186.

Body Composition, Energy Utilization, and Nitrogen Metabolism with a 4.25–MJ/d Low–Energy Diet Supplemented Pyruvate[1–3] Am J Clin Nutr 1992;56:630–5, 1992 American Society for Clinical Nutrition.

Enhancement of Arm Exercise Endurance Capacity with Dihydroxyacetone and Pyruvate 1061–7567/90 1990 the American Physiological Society.

Enhanced Leg Exercise Endurance with a High–Carbohydrate Diet and Dihydroxyacetone and Pyruvate 0161–7567 (1990) the American Physiological Society.

Reduction of Carcass Fat in Swine with Dietary Addition of Dihydroxyacetone and Pyruvate[1] J Anim. Sci 1989. 67:1272–1278.

(List continued on next page.)

*Primary Examiner*—Joseph McKane
*Assistant Examiner*—Jane C. Oswecki
*Attorney, Agent, or Firm*—Fay, Sharpe, Fagan, Minnich & McKee, LLP

[57] ABSTRACT

A pyruvate compound suitable for cosmetically or dermatologically administering to the skin and for use in treating diabetic ketosis or other medical treatments. The compound includes a pyruvate selected from the group of pyruvate thioester, dihydroxyacetonepyruvate, and an ester of pyruvate and a sugar or a polyol.

34 Claims, 17 Drawing Sheets

Cardiac Recovery after 25 min. Global Warm Ischemia

OTHER PUBLICATIONS

Body Composition, Energy Utilization, and Nitrogen Metabolism with a Severely Restricted Diet Supplemented with Dihydroxyacetone and Pyruvate[1-3] Am J Clin Nutr 1992;55:771–6 (1992) American Society for Clinical Nutrition.

Blood Glucose Extraction as a Mediator of Perceived Exertion During Prolonged Exercise.

European Journal of Applied Physiology and Occupational Physiolog (1990) 61:100–105.

Federation Proceedings, vol. 46, No. 7, May, 1987, "Free Radical Scavengers in Myocardial Ischemia", by Paul J. Simpson, et al.

Free Radical Biology & Medicine, vol. XX, No. X, 1995, "Effects of N–Acetylcysteine in the Rat Heart Reperfused After Low–Flow Ischemia: Evidence for a Direct Scavenging of Hydroxyl Radicals and a Nitric Oxide Dependent Increase in Coronary Flow" by Julie Brunet, et al.

Ann. Surg., vol. 209, No. 5, May, 1990, "Effect of Pyruvate on Regional Ventricular Function in Normal and Stunned Myocardium", by Mentzer, et al.

Molecular and Cellular Biochemistry, 22:93–100 "Effect of Pyruvate on Rat Heart Thiol Status During Ischemia and Hypoxia Followed by Reperfusion", by Maria Pia Rigonbello and Alberto Bindoli, Jan., 1993.

J. Thorac Cardiovasc Sug., 1991; 101:509–16, "Alcohol and Pyruvate Cardioplegia", by Ann Wikman–Coffelt, et al.

The New England Journal of Medicine, vol. 324, No. 26, "Improvement by Acetylcysteine of Hemodynamics and Oxygen Transport in Fulminant Hepatic Failure", by Phillip Harrison, et al., Jun., 1991.

Hart, Hart and Crane, Organic Chemistry, 9th Ed., 1995, p. 301.

MEDICAL USES OF PYRUVATES

CROSS-REFERENCE TO RELATED PATENT APPLICATION

This application is a continuation-in-part of U.S. Ser. No. 08/807,585 filed Feb. 27, 1997, now U.S. Pat. No. 5,876,916 which is a continuation-in-part of U.S. Ser. No. 08/617,285 filed Mar. 18, 1996, now U.S. Pat. No. 5,667,962 and claims the benefit of U.S. Provisional Application Ser. No. 60/046,343 filed May 13, 1997 and Ser. No. 60/080,695 filed Apr. 3, 1998.

BACKGROUND OF THE INVENTION

This invention relates to several new pyruvate compounds and methods of (i) treating ischemia in mammalian hearts, lungs, veins, arteries and other organs or tissues, (ii) accelerating ethanol oxidation/preventing acute toxic effects of ethanol on the liver, (iii) using the novel pyruvates in other recognized uses of pyruvates including, but not limited to, treating of secondary effects of diabetes, lowering of cholesterol and lipid levels, as a nutrition source which can provide as much as 100% of caloric requirements and to treat injured organs requiring a readily accessible energy source, (iv) topical applications of pyruvates in the treatment of dermatological wounds or diseases and prevention thereof and to generally improve skin health, and (v) treatment of diabetic ketosis.

DESCRIPTION OF THE ART

Ischemia is defined herein as the interruption of oxygen supply, via the blood, to an organ or to part of an organ. Examples of ischemic events include (i) myocardial, cerebral, or intestinal infarction following obstruction of a branch of a coronary, cerebral, or mesenteric artery, and (ii) removal and storage of an organ prior to transplantation. In the case of myocardial infarction, prompt restoration of blood flow to the ischemic myocardium, i.e. coronary reperfusion, is a key component of the treatment. This is because mortality is directly related to infarct size (tissue necrosed) which is related to the severity and duration of the ischemic event.

Notwithstanding the need to supply an organ cut-off from a normal blood supply with oxygen, it has been found that reperfusion injury may occur upon restoration of blood flow. This results from the production of reactive oxygen species (ROS), namely, hydrogen peroxide, hydroxyl radicals and superoxide radicals which are formed from both extracellular and intracellular sources. ROS are highly reactive species that, under normal conditions, are scavenged by endogenous defense mechanisms. However, under conditions of post-ischemic oxidative stress, ROS interact with a variety of cellular components, causing peroxidation of lipids, denaturation of proteins, and interstitial matrix damage, resulting in increase of membrane permeability and release of tissue enzymes.

In an attempt to minimize these undesirable side effects of perfusion, researchers Simpson, et al., (Free Radical Scavengers and Myocardial Ischemia, *Federation Proceedings*, Volume 46, No. 7 May 15, 1987) suggest the use of an inhibitor of ROS production to protect the reperfused myocardium. The Simpson, et al. disclosure is particularly directed to the use of agents and inhibitors (ex. allopurinol) that reduce ROS levels. In a similar context, Brunet, et al., (Effects of Acetylcysteine, *Free Radical Biology and Medicine*, Volume XX, No. X 1995) suggest the use of acetylcysteine to reperfuse hearts. In particular, the article concludes that acetylcysteine treatment decreases the production of ROS in reperfused rat hearts.

In a further effort directed to protecting reperfused heart tissue, U.S. Pat. No. 5,075,210, herein incorporated by reference, discloses a process for reperfusing a heart for transplantation. The patent discloses a cardioplegic solution containing sodium chloride, potassium chloride, calcium chloride, sodium bicarbonate, sodium EDTA, magnesium chloride, sodium pyruvate and a protein.

U.S. Pat. No. 5,294,641, herein incorporated by reference, is directed to the use of pyruvate to prevent the adverse effects of ischemia. The pyruvate is administered prior to a surgical procedure to increase a patient's cardiac output and heart stroke volume. The pyruvate is administered as a calcium or sodium salt. The pyruvate can alternatively be an ester of pyruvic acid such as ethylamino pyruvate. Similarly, U.S. Pat. No. 5,508,308, herein incorporated by reference, discloses the use of pyruvyl glycine to treat reperfusion injury following myocardial infarction.

U.S. Pat. Nos. 4,988,515 and 5,705,210, herein incorporated by reference, use pyruvate salts in cardioplegic solutions and in preservation solutions for the heart before transplantation. U.S. Pat. No. 4,970,143, herein incorporated by reference, discloses the use of acetoacetate for preserving living tissue, including addition of the pyruvate to the preservation solution.

U.S. Pat. No. 5,100,677 herein incorporated by reference, discloses the composition of various parenteral solutions. Of interest is a recommendation to include pyruvate anions (apparently from metal salts) in intravenous solutions. In U.S. Pat. No. 5,183,674, herein incorporated by reference, pyruvate compounds are used as foodstuff. U.S. Pat. No. 5,134,162 herein incorporated by reference, focuses on the use of pyruvate to lower cholesterol and lipid levels in animals. U.S. Pat. No. 5,047,427, deals with the use of pyruvate for improving the condition of diabetics, while U.S. Pat. No. 5,256,697 suggests the use of pyruvyl-aminoacid compounds, each of which is herein incorporated by reference.

In addition, U.S. Pat. No. 5,283,260, herein incorporated by reference, is directed to treatment of diabetes with a physiologically acceptable form of pyruvate. The patent discloses a pyruvate compound in the form of a covalently linked pyruvyl-amino acid. By utilizing this type of a pyruvate delivery system, the negative effect of pyruvate salt is avoided. However, administration of large amounts of pyruvate-amino acid may result in nitrogen overload which could harm patients with liver and/or kidney pathology.

Notwithstanding the acceptance of pyruvate as an effective component of a reperfusion solution or other varied applications, pyruvic acid is a strong and unstable acid which cannot be infused as such. Furthermore, it has been recognized that traditional pharmacological pyruvate compounds, such as salts of pyruvic acid, are not particularly physiologically suitable. For example, these compounds lead to the accumulation of large concentrations of ions (ex. calcium or sodium) in the patient's body fluids. Similarly, amino acid compounds containing pyruvate can lead to excessive nitrogen loads. It has also been proposed to infuse pyruvylglycine, the amide function of which is presumably hydrolyzed in plasma and/or tissues, thus liberating pyruvate. However, at the high rates of pyruvylglycine infusion required to achieve 1 mM pyruvate in plasma, the glycine load may be harmful to patients suffering from hepatic or renal pathologies. Also, flooding plasma with glycine may interfere with the transport of some amino acids across the blood-brain barrier. Accordingly, while potentially suitable to organ preservation, these pyruvate compounds are less suited to treating an organ in vivo, and it is recognized that a need exists to provide a pyruvate delivery compound which is more physiologically acceptable.

In addition, pyruvates have been demonstrated to have several dermatological uses. For example, U.S. Pat. Nos. 5,580,902; 5,602,183; and 5,614,561, herein incorporated by reference, disclose the use of pyruvate salts and ethyl ester to enhance therapeutic effects of cosmetics and pharmaceuticals. It is believed that the present pyruvate compounds are suited for at least all of the treatments identified in these patents and can be formulated into ointments, creams, etc., much in the same ways identified therein, and in other systems apparent to one skilled in the art.

Therefore, it is desirable in this field to have an alternate physiologically compatible therapeutic pyruvate compound. In this regard, the novel pyruvate compounds of this invention permit the use of pyruvate to treat ischemic events, ethanol poisoning, acetaminophen poisoning and other conditions recognized to be effectively treated with pyruvate because sufficiently high loads of pyruvate can be administered without a toxic constituent.

SUMMARY OF THE INVENTION

Accordingly, it is a primary object of this invention to provide a new and improved pyruvate compound(s).

It is an advantage of this invention to provide a new and improved method for organ reperfusion. It is still a further advantage of this invention to provide a new and improved method for treating ethanol intoxication. An additional advantage of this invention is to provide a pyruvate compound which can provide nutritional benefits.

To achieve the foregoing objects and in accordance with the purpose of the invention, as embodied and broadly described herein, one novel pyruvate compound of this invention comprises a pyruvate thioester. Preferably, the thiol is cysteine or homocysteine. In a particularly preferred form, the compound is a N-acetyl ethyl ester of the cysteine or homocysteine amino acid.

One preferred compound is:

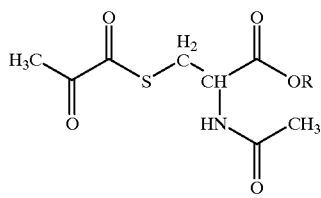

A further novel compound of the present invention is a glycerol-pyruvate ester. A particularly preferred form of a glycerol-pyruvate ester will be of the formula:

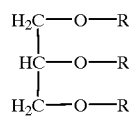

where one, two, or three R groups are pyruvyl

-continued

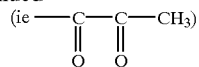

and one or two R may be a short-chain acyl such as acetyl or propionyl.

and more preferably

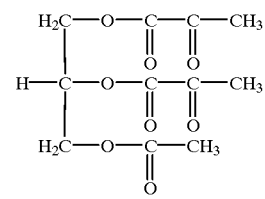

Another novel compound of the present invention is a dihydroxyacetone-pyruvate ester.

A particularly preferred form of this compound is of the formula:

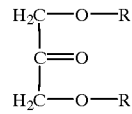

where one or two R groups are pyruvyl

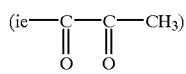

and one R may be a short-chain acyl such as acetyl or propionyl.

and more preferably

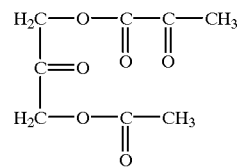

Another novel compound of the present invention is a ribose pyruvate ester. A particularly preferred form of this compound is of the formula:

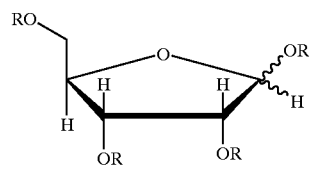

where R is H, pyruvyl, or a short-chain acyl such as acetyl or propionyl, not all four R's are H, one to four R's may be pyruvyl, and one to three R's may be short-chain acyl.

Another novel compound of the present invention is a glucose pyruvate ester. Particularly preferred forms of this compound (pyranose and furanose) are of the formulae:

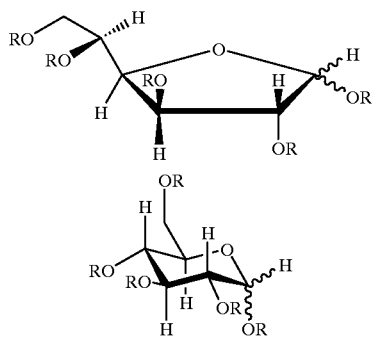

where R is H, pyruvyl, or a short-chain acyl such s acetyl or propionyl,
not all five R's are H,
one to five R's may be pyruvyl, and
one to four R's may be short-chain acyl.

The invention is also directed to use of the novel pyruvate compounds in reperfusion of tissue and organs both in vivo and in storage. Accordingly, the invention includes a method for the preservation of tissue deprived of oxygen through events including, but not limited to, coronary infarction, stroke, mesenteric infarction, organ transplant (during preservation and intravenously after grafting of the organ) including amputated limbs. The compound is also believed well suited to treatment of acetaminophen poisoning of the liver which depletes liver glutathione stores leading to acute hepatic necrosis.

This invention is also directed to the use of the novel pyruvate compounds to assist a patient's body in ethanol oxidation. In fact, the novel pyruvate compounds of this invention are suited to use as nutritional supplements, preventing body fat deposition, lowering high blood cholesterol levels, and treatment for secondary diabetes effects. Furthermore, the novel pyruvates are believed superior for use in treating alcohol intoxication, dermatological requirements and diabetic ketosis.

It is believed that pyruvate acts as a NADH trap and a trap for ROS generated upon reperfusion. In addition, the thiol group from cysteine, for example is believed to scavenge ROS. Similarly, the carbonyl group of dihydroxyacetone acts as a NADH trap. Accordingly, the subject novel compounds provide stable, and physiological compounds with the beneficial result of delivering pyruvate and an additional NADH and ROS trapping moiety.

BRIEF DESCRIPTION OF THE DRAWINGS

The invention consists of the novel parts, construction and arrangements, combinations and improvements shown and described. The accompanying drawings, which are incorporated in and constitute a part of the specification illustrate one embodiment of the invention and together with the description explain the principals of the invention.

Of the drawings.

DETAILED DESCRIPTION OF THE PREFERRED EMBODIMENTS

Figure 1:
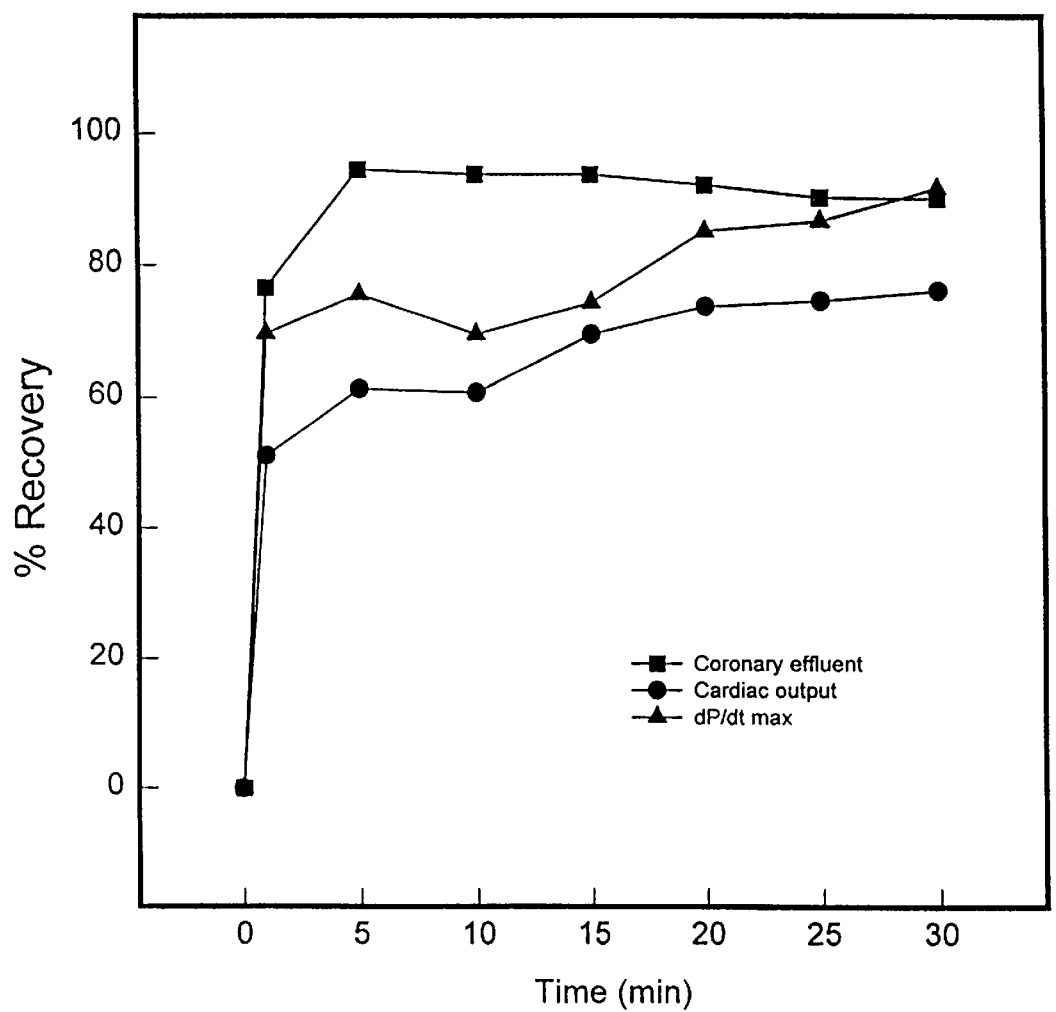
FIGS. 1 and 2 are graphical representations of the results of the experiments on ischemia of isolated rabbit hearts set forth hereinbelow.

For the purposes of this disclosure, the following abbreviations are used:

ADH, alcohol dehydrogenase; ALDH, aldehyde dehydrogenase; DCA, dichloroacetate; DHA, dihydroxyacetone; DHAP, dihydroxyacetone phosphate; DPAG, dipyruvyl-acetyl-glycerol; FAEE, fatty acid ethyl esters; GC, gas chromatography; GCMS, gas chromatography-mass spectrometry; LAD, left anterior descending coronary artery; MS, mass spectrometry; NAC, N-acetylcysteine; NEFA, non-esterified fatty acids; PADA, pyruvyl-acetyl-dihydroxyacetone; PDAG, pyruvyl-diacetyl-glycerol; PDH, pyruvate dehydrogenase; PNACE, pyruvate N-acetylcysteine ethyl ester; ROS, reactive oxygen species.

Reperfusion

As described above, timely coronary reperfusion as treatment for acute myocardial infarction reduces myocardial infarct size and improves survival rates. However, there is concern that reperfusion may cause further injury to the myocardium, called "reperfusion injury". More particularly, experimental studies have demonstrated that myocardium reperfused after reversible ischemia exhibits prolonged depression or "myocardial stunning". There is evidence that reperfusion of ischemic myocardium results in the generation of ROS and that a burst of ROS production at the time of reperfusion causes myocardial damage. Accordingly, attempts have been made to provide pyruvate compounds which trap and/or prevent the formation of ROS.

One form of the present invention is a novel compound including a pyruvate moiety which also traps reducing equivalents (NADH) and ROS, and a thiol moiety which traps ROS. Accordingly, the present compound provides dual functionality in an effective and highly efficient manner and in a physiologically soluble molecule. In addition, the compounds are degraded to physiological and safe metabolites (pyruvate, cysteine or homocysteine). Lastly, the present inventive compound is equally applicable to use in the preservation of organs removed for transplantation.

In summary, the novel compounds are redox chimeras whose molecules contain a trap for reducing equivalents (NADH) and a trap for ROS.

The inventive compounds demonstrate the following characteristics;

(i) water solubility;

(ii) no ionic charge, to facilitate diffusion through cell membranes and to avoid the need to administer a counter-ion, such as $Na^+$;

(iii) metabolizable to physiological compounds; and (iv) stability in solution.

PNACE

One preferred group of the inventive compounds is a thioester of pyruvate and a sulfur amino acid, for example cysteine or homocysteine. Preferably, any ionizable functions on the amino acid molecule are blocked by easily removable radicals, such as ethyl and N-acetyl groups. The most preferred compound is formed of pyruvate and N-acetylcysteine ethyl ester.

The invention will now be described with reference to the following examples, intended to describe, but not limit the invention.

Recovery of isolated rabbit hearts following 25 min of warm ischemia

Hearts were removed from anesthetized New Zealand rabbits (2.5–3.0 kg) and perfused in the working mode at 370 with non-recirculating Krebs-Ringer bicarbonate (KRB) buffer containing 5 mM glucose and 5 units/i of insulin, and equilibrated with a gas mixture containing 95% $O_2$+5% $CO_2$. In the working mode, which simulates physiological conditions, hearts pump the buffer against a 85 cm hydrostatic pressure in the aorta. The mechanical performance of the hearts was assessed by monitoring heart rate, cardiac output, coronary flow, left ventricular pressure, and $dP/dt_{max}$. The latter parameter reflects the capacity of the heart to increase hydrostatic pressure in the left ventricle.

Following 30 minutes of equilibration, the hearts were made ischemic for 25 minutes by clamping the aortic and left atrial canulas. Then, the clamps were removed to allow reperfusion with oxygenated KRB buffer containing either no additive (n=7, control group), or 20 μM pyruvate-N-acetyl-cysteine ethyl ester (PNACE) (n=7). PNACE was infused via a syringe pump into the inflowing perfusate. In the syringe, PNACE was dissolved in 0.1 mM HCl to prevent hydrolysis of the thioester.

None of the control group hearts recovered any function. In contrast, hearts reperfused with buffer containing 20 μM PNACE recovered 75 to 95% of their mechanical function after reperfusion was instituted (see FIGS. 1 and 2). Functional recovery lasted throughout the 30 minute reperfusion experiment.

Recovery of isolated rabbit hearts following massive catecholamine injury

Rabbit hearts were perfused in the working mode as in the above example. However, after the 30 minutes of equilibration, 50 μM isoproterenol was added to the inflowing perfusate for 10 min. Isoproterenol is a catecholamine, which, at the dose administered, induces a marked increase in heart rate and cardiac output. After 10 minutes, the mechanical performance of the hearts decreased markedly to the point where cardiac output was almost zero. Then, isoproterenol infusion was stopped, and perfusion was continued for 30 minutes with oxygenated KRB buffer containing either no additive (n=7, control group), or 20 μM PNACE (n=7). The hearts perfused with plain buffer did not show recovery of cardiac function. In contrast, hearts perfused with buffer containing 20 μM PNACE recovered 75 to 95% of their mechanical function.

Figure 2:
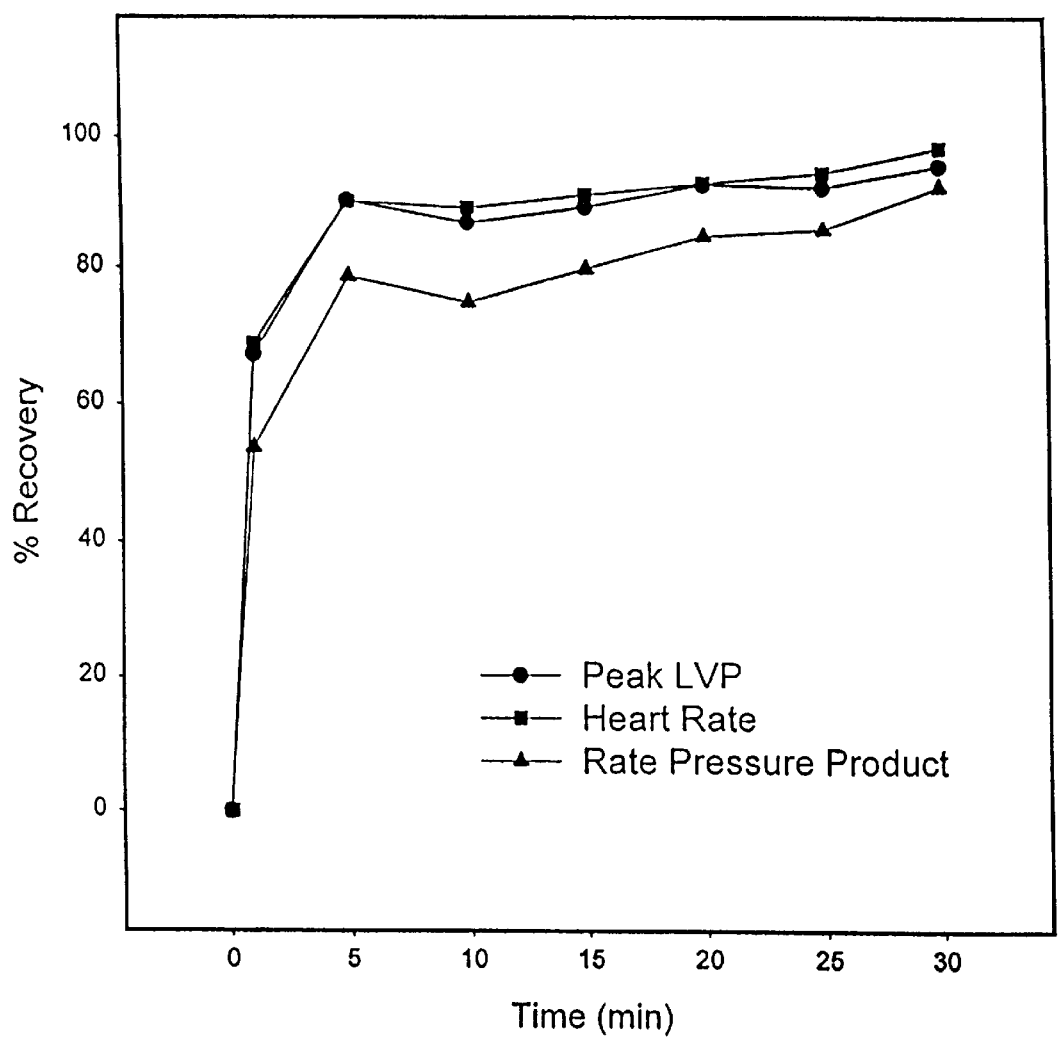

The data of these experiments proved substantially similar to that shown in FIGS. 1 and 2.

Improved function of preserved rat livers

Livers from overnight-fasted rats were surgically removed and flushed at 37° C. with non-recirculating KRB buffer containing 5 mM glucose and equilibrated with a gas mixture containing 95% $O_2$+5% $CO_2$. The first group of livers (n=7, control group) was not preserved, but was perfused at 37° C. for 45 minutes. The second group of livers (n=8, preserved group) was flushed with ice-cold University of Wisconsin (UW) preservation solution and stored for 24 hours in ice-cold UW solution. Next, the livers were reperfused at 37° C. with non-recirculating KRB buffer containing 5 mM glucose. The third group of livers (n=8, preserved+PNACE group) was treated as the second group except that 20 μM PNACE was added to the UW preservation solution and to the reperfusion KRB buffer. During the last 45 min of (re)perfusion, the function of the three groups of livers was assessed by (i) the release of three cellular enzymes, i.e. lactate dehydrogenase, aspartate aminotransferase, and alanine aminotransferase, (ii) oxygen consumption, and (iii) the production of ketone bodies, ie β-hydroxybutyrate+acetoacetate, after addition of 1 mM octanoate to the perfusate.

The data depicted in Table I, show that, in preserved reperfused rat livers, PNACE (i) markedly decreases the initial release of tissue enzymes, (ii) restores partially the capacity of the liver to oxidize fatty acids to ketone bodies, and (iii) restores oxygen consumption to the level of non-preserved livers.

Effect of PNACE on metabolic integrity of preserved rat livers upon reperfusion

All data from group III are statistically different from the corresponding data of group II.

TABLE 1

| Parameter measured | Group I Control non-preserved (7) | Group II Control preserved (8) | Group III Preserved + PNACE (8) |
|---|---|---|---|
| Release of lactate dehydrogenase (U/L.g) 10–14 min. | 1.9 | 21.8 | 4.5 |
| Release of aspartate amino-transferase (U/L.g) 25–30 min. | 0.28 | 3.4 | 0.73 |
| Release of alanine aminotransferase (U/L.g) 25–30 min. | 0.21 | 3.7 | 0.33 |
| Ketone body production (μmol/min.g) 25–30 min. | 3.1 | 0.9 | 1.4 |
| Oxygen consumption (μmol/min.g) 25–30 min. | 2.1 | 1.3 | 2.4 |

Synthesis of PNACE

As understood in the art, pyruvate has proven to be a relatively unstable compound with very limited mechanism for satisfactory delivery to subjects.

However, the present inventive compound has proven to be readily manufacturable and very effective in the prevention of organ damage associated with reperfusion injury. The compound has been prepared in pure form and in gram amounts. Its formula has been confirmed by elemental analysis and gas chromatography-mass spectrometry. The compound is stable in slightly acidic solutions (pH 4–5). At pH 7.4, it is slowly hydrolyzed to pyruvate and N-acetylcysteine ethyl ester. The compound has also been synthesized labeled with three deuterium $^2H$ atoms on the N-acetyl moiety. This deuterated compound is used as an internal standard for the assay of the compound by isotope dilution gas chromatography-mass spectrometry.

In a three-neck flask of 500 ml, freshly distilled pyruvic acid (9.06 g., 0.102 mol) and N-hydroxy-succinimide (11.82 g., 0.102 mol) in dry tetrahydrofurane (THF) (180 ml) was stirred under nitrogen and was cooled in a ice bath. Dicyclohexylcarbodiimide (21.2 g., 0.102 mol) dissolved in dry THF (150 ml) was added slowly to the stirred cooled mixture over approximately 1 hr. Then, the reaction mixture was stirred at room temperature for 2.5 hr, followed by slow addition of N-acetyl-L-cysteine ethyl ester (6.81 g., 0.033 mol) dissolved in 20 ml dry THF over approximately 1 hr. The reaction mixture was stirred overnight at room temperature under a nitrogen atmosphere.

After evaporating the THF, the residue was suspended in ethyl acetate (750 ml) and was kept for 4–6 hr at 0° C. Dicyclohexyl urea (DCU) was then filtered and discarded; the ethyl acetate solution was washed three times with water (3×10 ml). It was then dried over anhydrous sodium sulfate and concentrated under vacuum.

The product (17–18 g.) was further purified by using column chromatography. A column of 5 cm. diameter was filled with silica gel (180–200 g., 60 Angstrom flash chromatography from Aldrich). The product was dissolved first in a minimum quantity of ethyl acetate:hexane (60:40) and was loaded on the column. The column was developed under gravity (rather than flash chromatography) with ethyl acetate:hexane (60:40). Fifty ml fractions were collected and monitored by TLC using either iodine or UV light. The fractions containing the product were combined and solvents were removed under reduced pressure. The residue was dissolved in chloroform (300 ml), first washed with 5% HCl (2×30 ml) and then saturated NaCl (3×60 ml). The organic layer was dried over anhydrous sodium sulfate, filtered, and the solvent evaporated. The residue was dissolved in a minimum quantity of chloroform, and petroleum ether was added until the solution became turbid. The suspension was kept overnight in the refrigerator and then filtered to get the pure crystallized product. The compound was dried under vacuum over $P_2O_5$ to a yield of 6.5 g. (75%, based on the N-acetyl-L-cysteine), m.p. 76–77° C.

Alternative synthesis of PNACE

To a 250 ml three neck flask fitted with a thermometer, a magnetic stirrer, a 50-ml pressure-compensated addition funnel, and a Friedrich's condenser under nitrogen, was added 10 g (52.3 mmoles) of N-acetyl-L-cysteine ethyl ester, 8.0 ml of dry pyridine and 60 ml of dry benzene.

Pyruvoyl chloride (0.104 mole, 2 eq) was added dropwise over a period of 0.5 hr. while maintaining a temperature of 5° C. to 10° C. Then, the reaction mixture was allowed to warm to 25° C. and stirred for 2 hours at this temperature. The benzene solvent was then evaporated under vacuum. The crude product was purified as above to yield 11.15 g of the desired compound (82%).

Synthesis of Deuterated PNACE

Pyruvate-N-[$^2H_3$]acetyl-L-cysteine ethyl ester

Synthesized wherein the above procedure was followed using N-[$^2H_3$] acetyl-L-cysteine ethyl ester to form ($d_3$-PNACE). The latter was prepared by reacting L-cysteine ethyl ester with [$^2H_6$]acetic anhydride.

Set forth hereinbelow are certain analytical characteristics of the composition of the invention provided to facilitate identification thereof, but not intended to limit the scope.

Characteristics of Compounds

I. Pyruvate-N-acetyl-L-cysteine ethyl ester: PNACE (unlabeled)

mp: 65° C.

Rf (ethyl acetate/petroleum ether: 3/2): 0.52

IR (Nicolet 300, $CCl_4$) ($cm^{-1}$):

3435 ($\upsilon$ N—H)

3000 ($\upsilon$ C—H)

1747 ($\upsilon$ CO—O) ester 1731 ($\upsilon$ CO—S) thioester 1687 ($\upsilon$ CO—CO,CO—N) ketoester, amide 1497, 1378.3, 1210.1

| NMR $^1H$, 300 MHz Varian, $CDCl_3$, TMS) (ppm): | NMR $^{13}C$, 100.12 MHz (Bruker, $CDCl_3$, TMS) (ppm): |
|---|---|
| 1:33(t, $^3J$=7.13, 3H, $OCH_2CH_3$) | 190.6; 188.08 keto, ketoester |
| 2.10(s, 3H, $COCH_3$) | 168.6, 168.08 ester, amide |
| 2.50(s, 3H, $CH_3COCO$) | 60.1($OCH_2$) |
| 3.45(dd, $^3J$=4.10Hz, $^3J$=8.95Hz, 2H, $CH_2$—S) | 49.5($CH_2S$) |
| 4.23(dd, $^3J$=7.13Hz, 2H, $CH_2CH_3$) | 28.4(CHNH) |
| 4.83(m, 1H, CH) | 21.9($CH_3COCO$) |
| 6.50(sl, 1H, NH) | 20.8($CH_3CO$) |
|  | 12.1($CH_3CH_2$) |
| Mass spectrum, electron ionization (m/z): | Mass spectrum, ammonia chemical ionization (m/z): |
| 190(M-$CH_3COCO$, 33); 118(26); 102(56); 76(33); 60(90); 43($CH_3CO^+$, 100) | 279(M+18, 100); 262(M+1, 93); 209(49); 192(60) 175(18), 158(26) |

II. Pyruvate-N-[$^2H_3$]acetyl-L-cysteine ethyl ester: $d_3$-PNACE (deuterated)

| NMR $^1H$, 300 MHz (Varian, $CDCl_3$, TMS) (ppm): | NMR $^{13}C$, 100 MHz (Brucker, $CDCl_3$, TMS) (ppm): |
|---|---|
| 1.34(t, J=7.13, 3H, $OCH_2CH_3$) | 190.5; 187.08 keto, ketoester |
| 2.50(s, 3H, $CH_3COCO$) | 168.5, 168.10 ester, amide |
| 3.42(dd, $^3J$=4.10Hz, $^3J$=8.95Hz, 2H, $CH_2$—S) | 60.1($OCH_2$) |
| 4.25(dd, $^3J$=7.13Hz, 2H, $CH_2CH_3$) | 49.1($CH_2S$) |
| 4.90(m, 1H, CH) | 28.1(CHNH) |
| 6.50(sl, 1H, NH) | 20.8($CH_3COCO$) |

| | |
|---|---|
| | 19.9($CD_3CO$)<br>12.0($CH_3CH_2$) |
| Mass Spectrum, electron ionization (m/z): | Mass spectrum, ammonia chemical ionization (m/z): |
| 193(M–$CH_3COCO$, 17); 121(4); 103(29); 77(12); 63(26); 43($CH_3CO$, 100) | 282(M+18, 42); 265(M+1, 47); 212(23), 195(37); 178(53); 161(100); 106(23); 89(15) |

Ethanol Metabolism

The following is believed to represent aspects of the human system for ethanol oxidation, but is supplied only as a representation of the theory, and is not intended to limit the invention in any way.

Ethanol is oxidized to acetate in the liver and the stomach by two reactions catalyzed by alcohol dehydrogenase (ADH) and aldehyde dehydrogenase (ALDH) which use $NAD^+$ as coenzyme. The bulk of ADH activity is in the liver. ALDH activity appears to occur in most tissues.

The ADH reaction is reversible; the mid-potential of the ethanol/acetaldehyde couple is –230 mV, which is very close to that of the lactate/pyruvate couple (–225 mV). In the absence of ALDH, the plasma ethanol/acetaldehyde ratio would be similar to the lactate/pyruvate ratio (about 10). However, the equilibrium of ADH is displaced by ALDH, the equilibrium of which is far toward acetate because of the very negative mid-potential of the acetaldehyde/acetate couple (–265 mV). As a result, the ethanol/acetaldehyde ratio is very high (>1000) and the acetaldehyde concentration difficult to measure (in the low $\mu$M range) unless ALDH is inhibited by disulfiram. In this invention, strategies for accelerating ethanol oxidation target the ADH pathway, but may have an impact on some of the toxic effects derived from non-ADH pathways.

Ingestion of alcoholic beverages leads to ethanol concentrations in body fluids that are much higher than the Km of liver ADH for ethanol. For example, in many US states, the legal limit of blood ethanol concentration compatible with driving a car, is 0.75 g/l or 17 mM. Drunkenness occurs at concentrations above 30 mM, and alcoholic coma at variable concentrations above 40 mM.

Reducing equivalents generated in the cytosol by ethanol oxidation are transferred to the mitochondria via the malate/aspartate and the citrate/malate shuttles. In mitochondria, reducing equivalents are oxidized in the respiratory chain. Ethanol oxidation can be seen as a sequence of three processes catalyzed by ADH, the reducing equivalent shuttles and the respiratory chain. It is possible to set up in vitro conditions where ethanol oxidation is limited either by ADH, the shuttles or the respiratory chain. However, in the intact in vivo liver, ethanol oxidation appears limited by the capacity of the respiratory chain to oxidize reducing equivalents, which itself is set by the ATP turnover. Under extreme conditions, most of the liver $O_2$ uptake is used to oxidize the reducing equivalents derived from ethanol.

Since the rate of ethanol oxidation is limited by the ATP turnover, an increase in this turnover raises the capacity to oxidize ethanol. In chronic ethanol ingestion (before liver decompensation), hyperthyroidism and chronic exposure to cold, the liver ATP turnover and the capacity of ethanol oxidation increase. In fact, a single gavage of ethanol induces (i) an increase in the rate of $O_2$ uptake by the rat liver perfused in the absence of ethanol, and (ii) an increase in the in vivo capacity of rats and humans to oxidize a second dose of ethanol.

In isolated livers, one can accelerate ethanol oxidation by imposing a drain on ATP with ureogenic substrates ($NH_4Cl$+ornithine+asparagine for example), gluconeogic substrates or uncoupler of the respiratory chain. In dogs, an intragastric gavage of $NH_4HCO_3$ increases the rate of ethanol oxidation. However, the toxicity of uncouplers precludes their use in vivo.

The liver of an adult human accounts for only 2% of body weight. However, the liver receives 100% of water-soluble nutrients absorbed from the gut. In addition, it must handle part of the lipid material (i) absorbed from the gut via the lymphatic system and (ii) released by adipose tissue lipolysis. Only a small fraction of nutrients' energy is used in the liver. Most of this energy is exported as substrate molecules to peripheral tissues.

The $O_2$ uptake of the 1.5 kg liver of a 75 kg subject is about 3 mol/day. Thus, the maximum ATP production of the liver is 18 mol/day. If all this $O_2$ uptake were used to oxidize ethanol to $CO_2$, only 1.1 mol of ethanol (51 g) could be oxidized per day. This would leave no room for (i) the obligatory hepatic ATP production from protein catabolism, (ii) ATP production from carbohydrate and fat catabolism. The liver manages this energy plethora by exporting most of the potential energy of ethanol as acetate, thus decreasing by 80% the hepatic ATP production from ethanol. Acetate is well used in peripheral tissues.

While most ethanol can be exported from the liver, there is no large-scale mechanism for exporting reducing equivalents from the liver. One obvious export mechanism would (i) trap reducing equivalents in the conversion of pyruvate to lactate, and (ii) export lactate to peripheral tissues. However, plasma pyruvate concentration is very low (0.05–0.1 mM). Pyruvate could be generated from glucose and amino acids, but these processes would further increase the liver's ATP burden. For these reasons the exogenous pyruvate compounds of the present invention are particularly suited to assist the body with ethanol oxidation.

The unregulated production of reducing equivalents in the liver increases the cytosolic and mitochondrial [NADH]/[$NAD^+$] ratios. This redox shift inhibits gluconeogenesis from proteins and the recycling of glucose in the Cori cycle by displacing the equilibrium of lactate, malate and α-glycero-P dehydrogenases. If the hepatic glycogen reserves are exhausted (for example after more than 12 hr of fasting), inhibition of gluconeogenesis can induce alcoholic hypoglycemia which can lead to hypoglycemic coma, brain damage and death. In addition, the redox shift inhibits the citric acid cycle at a-ketoglutarate dehydrogenase, lowering $CO_2$ production and the respiratory quotient sometimes to almost zero. Then, all the liver $O_2$ uptake is used to oxidize the reducing equivalents derived from ethanol.

Other processes are involved in the hepatic toxicity of ethanol: binding of acetaldehyde to proteins, damage to proteins by free radicals (superoxide, hydroxyl) probably generated by cytochrome P450 IIE1, which is induced by chronic alcohol ingestion. There is evidence that ethanol generates pro-oxidant reactive species in both the liver and the central nervous system. This leads to depletion of glutathione and to the covalent binding of hydroxyethyl radicals to liver microsomal proteins. Free radical damage and malnutrition are most likely implicated in the cirrhotic process.

Fatty acid ethyl esters (FAEE) have been identified in liver and in organs where oxidative metabolism of ethanol is minimal or absent, but which are commonly damaged by ethanol abuse: brain, pancreas, myocardium, and in cells cultured in the presence of ethanol. FAEE are formed by a synthase and an acyl-CoA:ethanol acyltransferase activity present in microsomes and cytosol of these organs. FAEE synthase activity is also present in white blood cells. After ethanol ingestion, FAEE are found in LDLs. Serum FAEE concentrations, assayed by GCMS, correlate with ethanol concentration. The half-life of plasma FAEE is ~1 min; they undergo hydrolysis in plasma and uptake by organs. FAEE bind to myocardial mitochondria in vitro and in vivo. The mitochondria hydrolyze FAEE to fatty acids, which are uncouplers of oxidative phosphorylation. This may account for the impaired mitochondrial function and inefficient energy production associated with the toxic effects of ethanol on the heart. Also, the accumulation of FAEE in embryos of rats given ethanol has been linked to the fetal-alcohol syndrome.

Amethystic agents could be used to treat alcoholic coma. Ethanol concentrations are typically in the 50 to 70 mM range. This condition is life threatening because it can mask alcoholic hypoglycemia leading to brain damage and possibly death. In addition, anesthesia of the respiratory center by ethanol depresses respiration and coughing, leading to respiratory acidosis and pulmonary infection. Sometimes, respiratory depression leads to respiratory arrest. Also, general alcoholic anesthesia induces hypothermia which itself can be lethal. Patients in alcoholic coma brought to the Emergency Room could be infused with amethystic agents until they regain some consciousness and show no depression of respiration. Similarly, if safe oral amethystic agents were available, their ingestion between alcoholic drinks, or sometimes before driving an automobile, could dramatically decrease the rate of accidents or violence while under the influence.

Ethanol oxidation in liver is limited by the capacity of the respiratory chain to oxidize reducing equivalents derived from the conversion of ethanol to acetate. The administration of pyruvate will accelerate ethanol oxidation by exporting the reducing equivalents in the form of lactate. This export will shift the burden of disposing of reducing equivalents from the liver (2% of body weight) to the bulk of peripheral tissues. Lactate is well used by peripheral tissues, particularly by muscle and kidney. In these tissues, lactate oxidation to $CO_2$ will probably result in an underutilization of fatty acids, glucose and glycogen. The notion of Cori cycle, in which lactate derived from glycolysis in erythrocytes is recycled to glucose in the liver, does not exclude oxidation of a large fraction of this lactate in peripheral tissues.

Pyruvic acid is a strong, unstable ketoacid which cannot be administered orally or parenterally. Sodium pyruvate is stable in dry form and could be dissolved as an isotonic solution just before use. However, the sodium and water loads would most likely kill the patient. The effects of the sodium load is compounded by the difference between the volumes of distribution of sodium (20% of body wt) and of ethanol (67% of body wt). Consider a numerical example: suppose we want to decrease the ethanol concentration by 20 mM in a 75 kg patient. The ethanol pool must decrease by 20×75×0.67=1,000 mmol. Since the oxidation of 1 mol ethanol generates 2 NADH, we need to supply 2×1,000=2,000 mmol of sodium pyruvate as 2,000/150=13.3 liters of isotonic solution (150 mM). Such volume cannot be administered safely. In addition, the 2,000 meq of sodium supplied is similar to the patient's original sodium pool: 140×75× 0.2=2,100 meq. Therefore, sodium pyruvate cannot be used.

However, unlike pyruvic acid, esters of pyruvate are stable. Esters of glycerol and/or dihydroxyacetone are preferred forms of amethystic agents for this invention. The ester will be hydrolyzed to pyruvic acid by non-specific esterases present in plasma, tissues and the gastrointestinal tract. Pyruvic acid will be neutralized by the body's buffers. Then, pyruvate will be reduced in the liver to lactate which will be oxidized to $CO_2$ in peripheral tissues. Overall, the strong pyruvic acid will be replaced by a weak acid which is eliminated by the lungs. From an acid-base point of view, this is similar to the oxidation to $CO_2$ of neutral compounds such as glucose and triacylglycerols. These oxidations pass through strong acids: pyruvic, lactic, acetoacetic and R-β-hydroxybutyric which are converted to weak and volatile $CO_2$. Thus, as long as the rate of pyruvate ester infusion matches the capacity of peripheral tissues to oxidize lactate, the concentration of the latter could be kept at a safe level (<10 mM), without major acid-base disturbance. The transient increase in the anion gap would not be greater than what occurs after strenuous muscular exercise.

DPAG and PADA

A second set of the inventive compounds are dipyruvyl-acetyl-glycerol (DPAG) and pyruvyl-acetyl-dihydroxyacetone (PADA). As with PNACE, these compounds are metabolizable substrates which counteract the effects of reperfusion injury. Glycerol is a physiological substrate which is well tolerated in large amounts and although DHA is not known to exist as such in body fluids, it is quickly phosphorylated by liver glycerol kinase to dihydroxyacetone phosphate (DHAP) which is a glycolytic intermediate. Similarly DPAG and PADA can be infused in vivo to deliver a therapeutic concentration of pyruvate without lactic acidosis and sodium overload. However, because DPAG and PADA can be administered in very high doses, they are also agents for accelerating ethanol oxidation in the liver, via transfer of reducing equivalents to peripheral tissues in the form of lactate.

Glycerol is a physiological substrate. It is released by adipose tissue lipolysis and is taken up by the liver, which is the major site of glycerol kinase activity (some glycerol kinase is also present in kidney). Glycerol kinase generates glycerol-phosphate which has 3 fates: glucose, glycerides/phospholipids, and lactate. DHA is converted to physiological dihydroxyacetone-phosphate (DHAP) by glycerol kinase. Then, DHAP has the same fates as glycerol. DHA is the oxidized counterpart of glycerol.

The rate of administration of pyruvate esters should be adjusted to keep lactate concentration below 10 mM. Such lactate concentrations, in the 5 to 10 mM range, favor the competition for oxidation with other fuels such as fatty acids and glucose. One can favor lactate oxidation by infusing a small amount of dichloroacetate (DCA, final concentration 1 mM), an activator of pyruvate dehydrogenase (PDH). This drug is used for the treatment of various types of lactic acidosis, in particular those resulting from congenitally low activities of PDH in peripheral tissues.

Because of the particular benefits of the thiol in PNACE, a dual strategy to prevent and/or treat reperfusion injury is considered advantageous. Moreover, to safely deliver large amounts of pyruvate without sodium or nitrogen load, esters of pyruvate with either glycerol or dihydroxyacetone, i.e. DPAG or PADA can be used. PNACE is not a means to supply large amounts of pyruvate, since pharmacologically NAC concentrations of below 0.1 mM are often desirable, while effective pyruvate concentrations are 1–2 mM. Thus, pyruvate-glycerol or pyruvate-DHA ester is infused in large amounts together with smaller amounts of PNACE.

Alternative, Suitable Pyruvate Ester Compounds

Also envisioned with in the context of this invention are pyruvate ester compounds comprised of physiologically suitable sugars and polyols, including but not limited to ribose, galactose, glucose, fructose, sorbitol, inositol, arabitol, erythritol and other polyols. Within this group, ribose and glucose are particularly preferred. Particularly esters of the formulae:

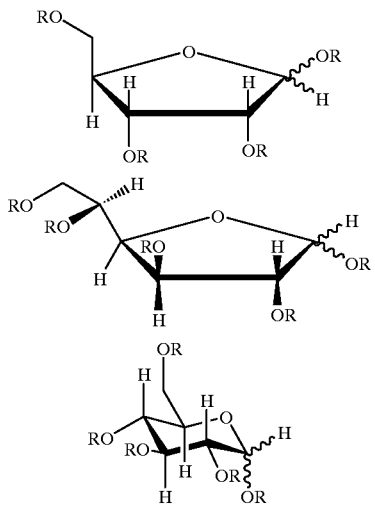

where R is H, pyruvyl or a short-chain acyl such as acetyl or propionyl and at least one R is pyruvyl.

Decrease in myocardial infarct size in swine by DPAG.

Figure 11:
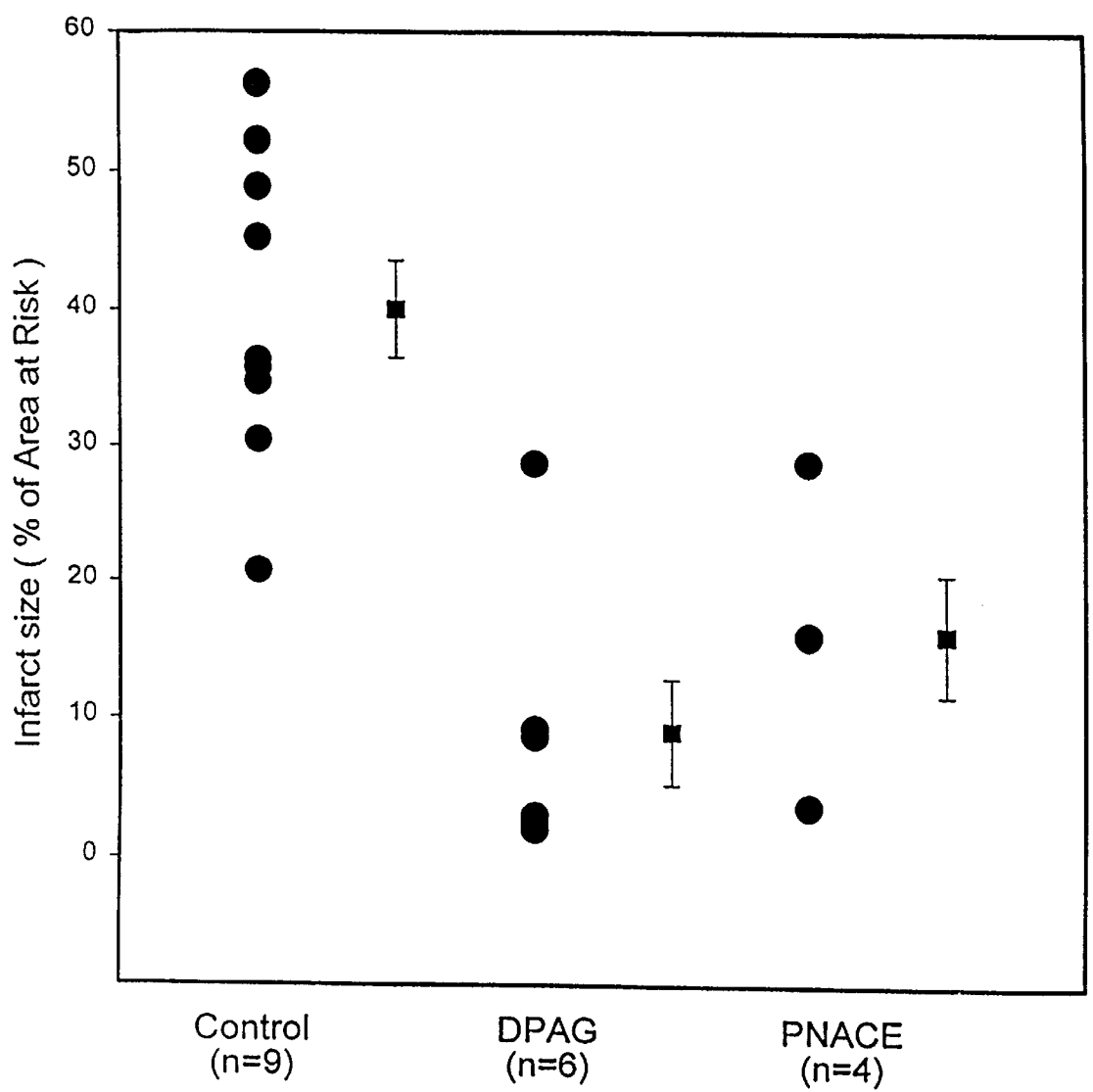
FIG. 11 shows swine infarct size after PNACE and DPAG treatment.
Figure 12:
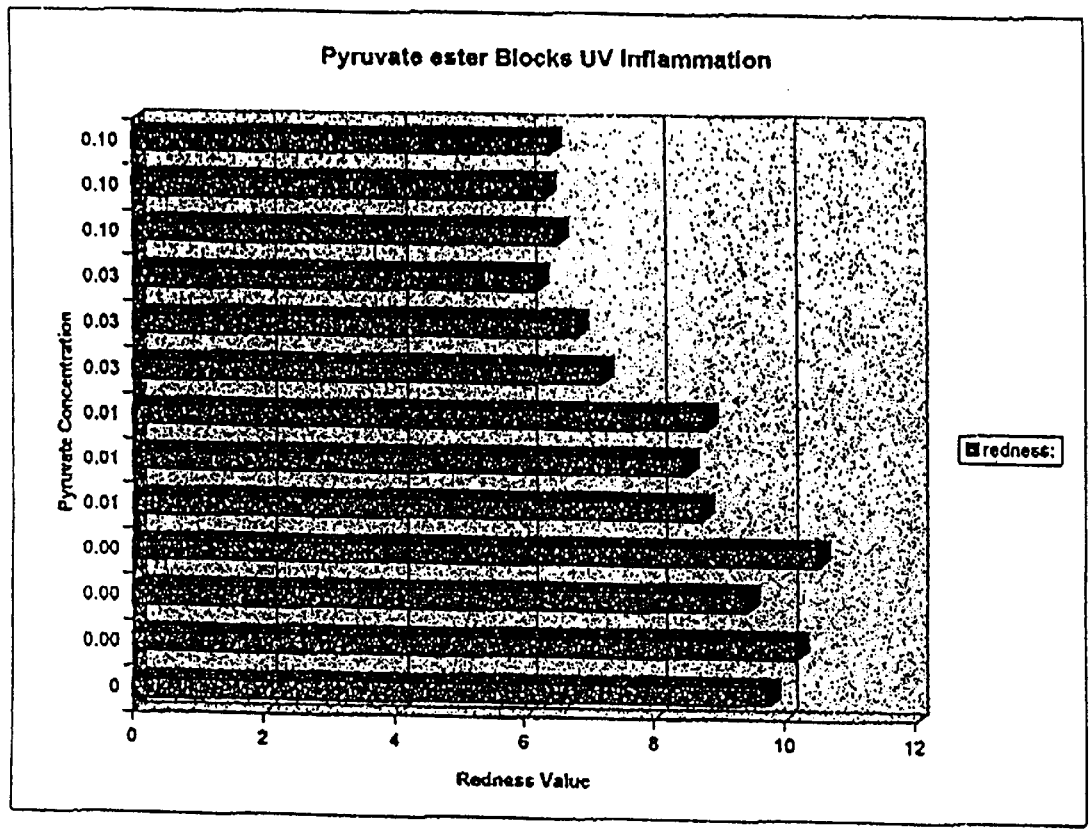
FIGS. 12, 13 and 15 show pyruvate ester blocking of UV inflammation.
Figure 13:
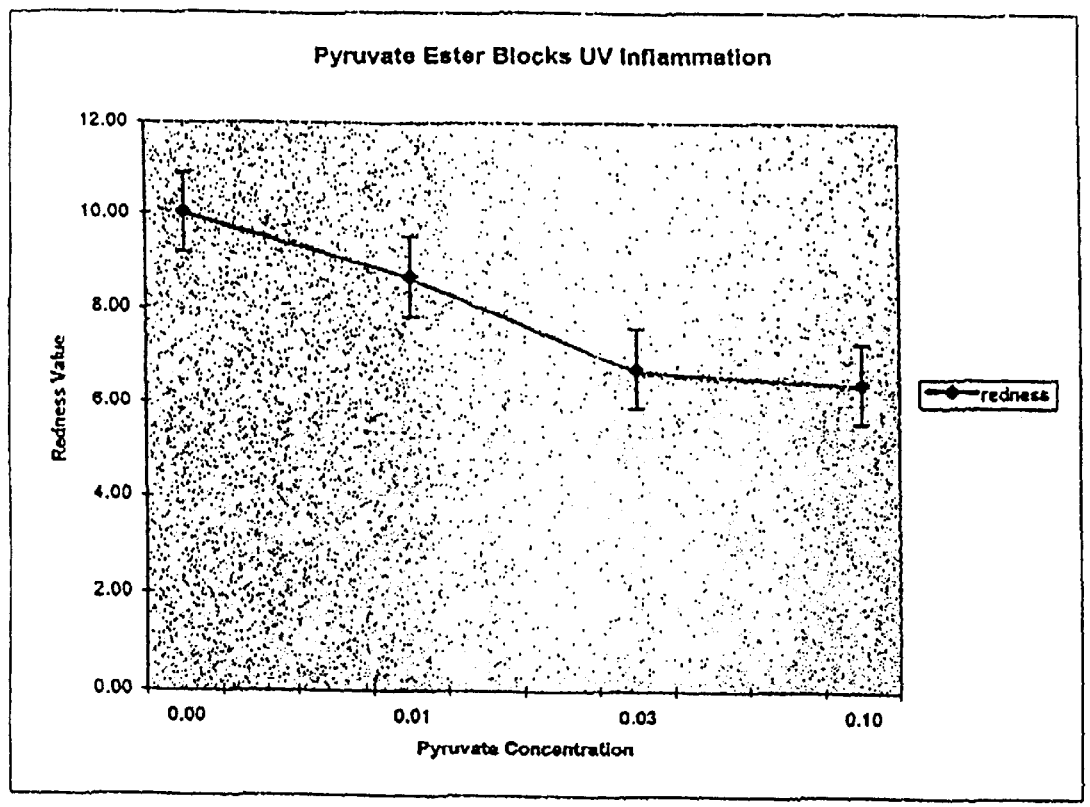
Figure 14:
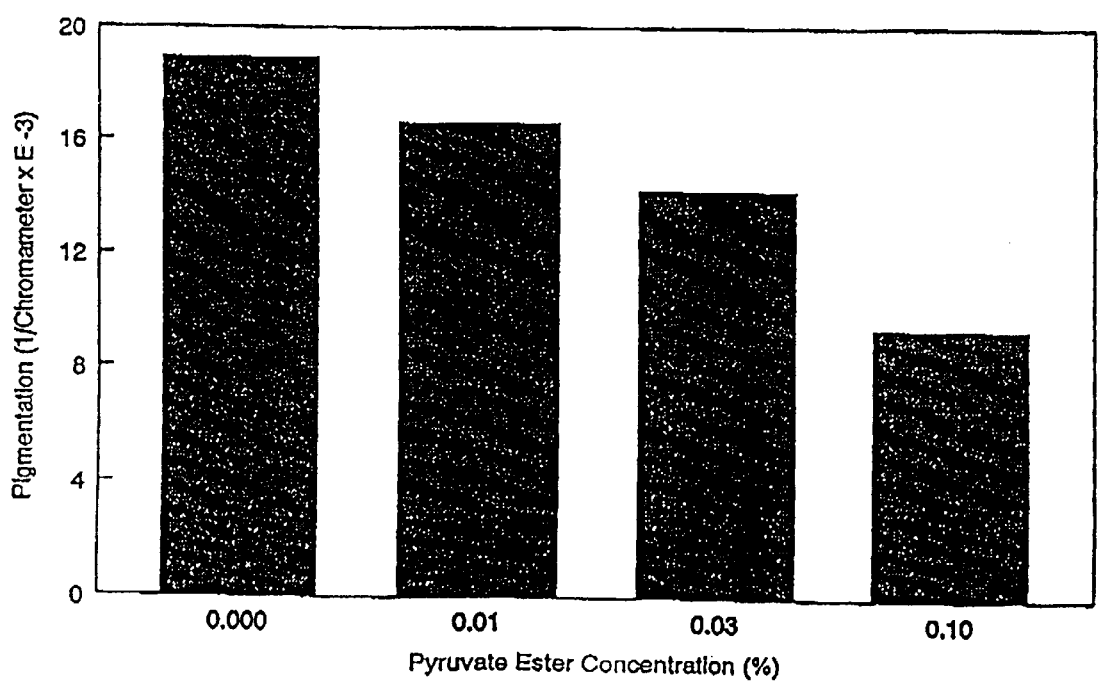
FIG. 14 shows pyruvate ester effect on UV pigmentation.
Figure 15:
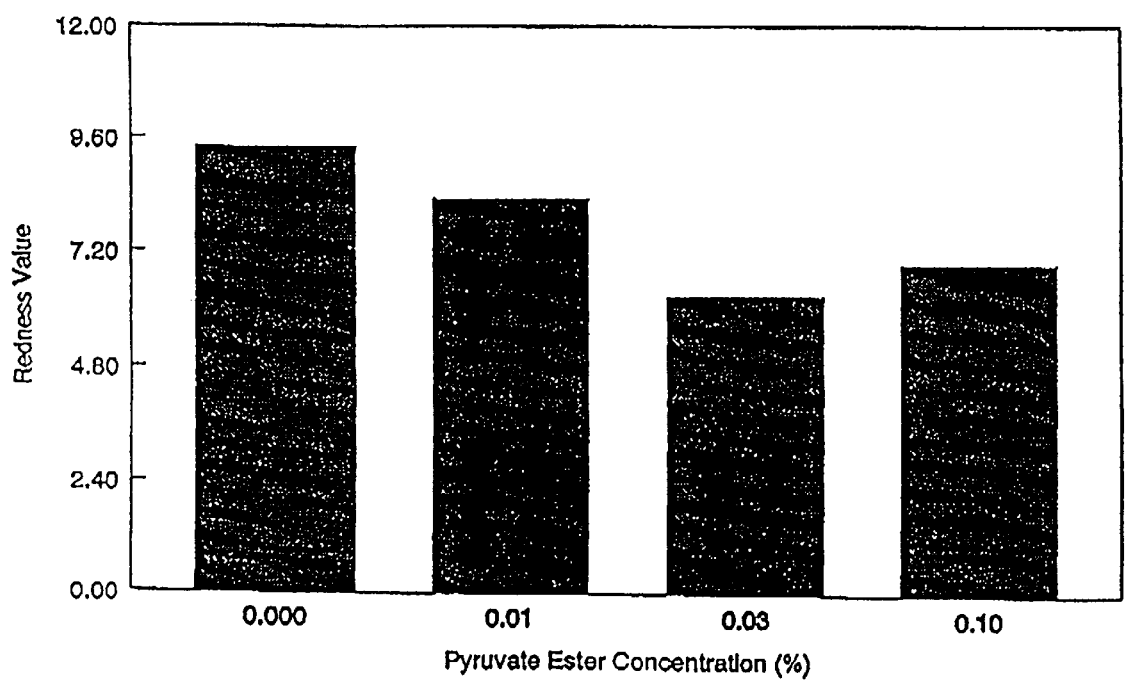
Figure 16:
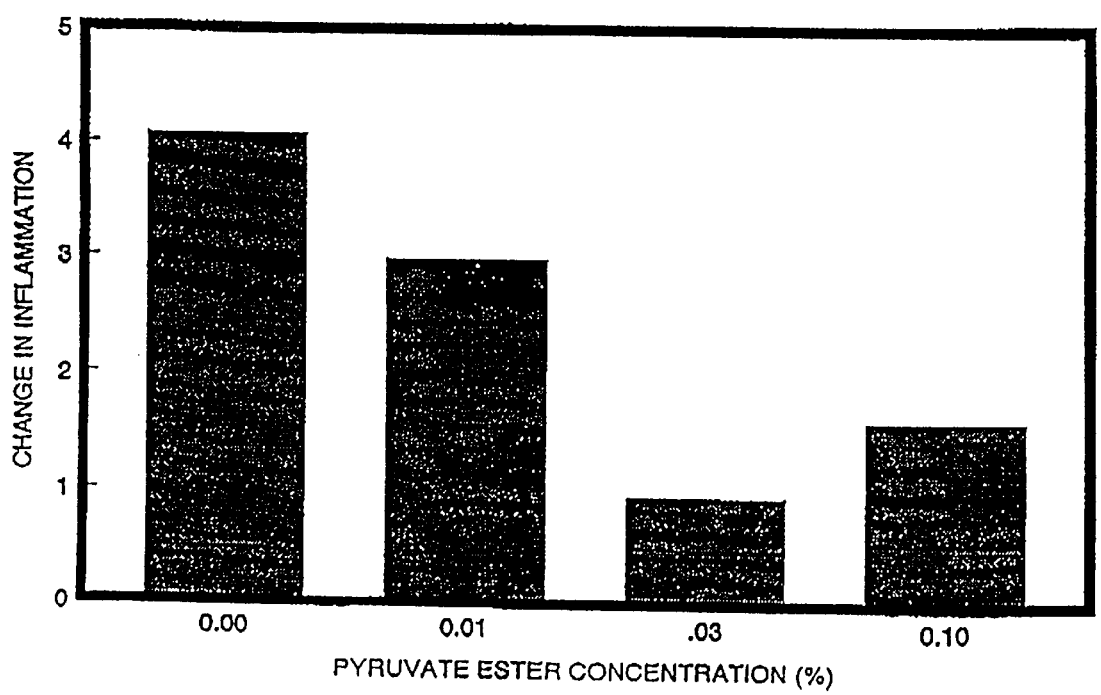
FIG. 16 shows pyruvate ester relationship to inflammation.

The animals were anesthetized, instrumented, and subjected to 60 minutes of total occlusion of the distal ⅔ of the left anterior descending coronary artery, followed by 120 min of reperfusion. The area of the infarct was stained with tetrazolium, and infarct size quantitated on 5 mm slices of tissue. Treatment with DPAG was started with the onset of reperfusion (8.0 mg/kgmin for 120 min). DPAG did not affect heart rate or ventricular pressure. Infarct size, expressed as a percent of the area at risk for infarction, was 40.0±3.6% in the control group (n=9), which compares favorably with recently published values from another laboratory using the same swine model (38.6±2.6%). with reference to FIG. 11, the DPAG treated group (n=6) had an infarct size of 9.1±3.8%, which was statistically lower than the control group (p<0.0005 by t-test). This demonstrated that DPAG, infused upon reperfusion, decresases markedly the size of myocardial infarct. A PNACE group (n=4) had an infarct size of about 16±4%.

Acceleration of ethanol oxidation

Rat livers were infused with ethanol and the components of the esters of glycerol-and-DHA pyruvate to represent the conditions that will occur after ester hydrolysis. Livers from 24 h-fasted rats were perfused with non-recirculating buffer containing 4 mM glucose and 2 mM ethanol (20 times the Km of ADH for ethanol, to insure zero order kinetics). After 10 min baseline, the influent perfusate was enriched with various equimolar concentrations of the components of the esters, ie DHA+Na-pyruvate, or glycerol+Na-pyruvate (up to 2.2 mM). These conditions simulated infusion and hydrolysis of glycerol- or DHA-monopyruvate. The uptakes of ethanol, pyruvate, DHA and glycerol, as well as the productions of lactate and glucose were measured.

Figure 3:
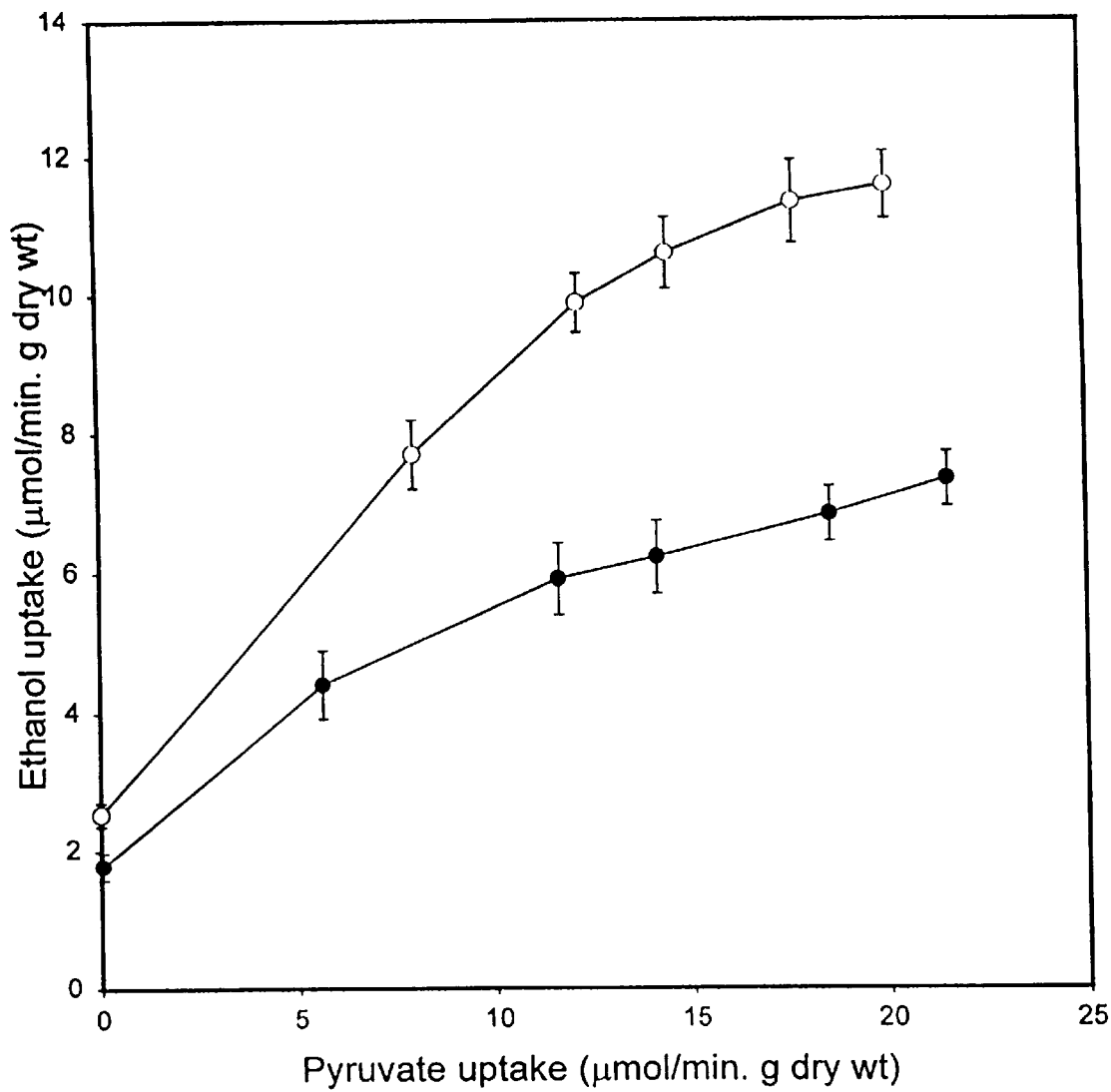
FIGS. 3-7 show the results of experiments or ethanol oxidation in livers.
Figure 4:
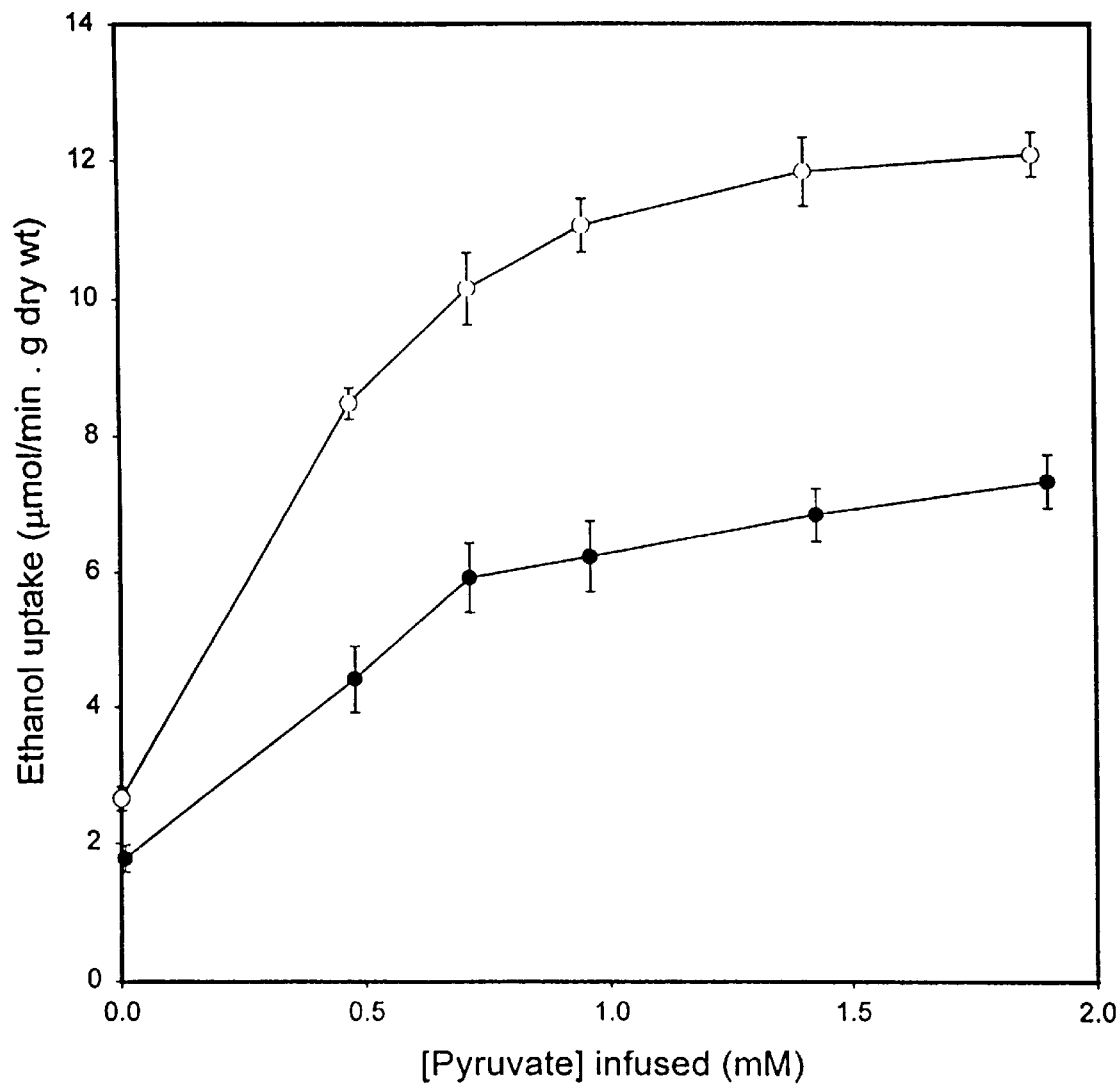
Figure 5:
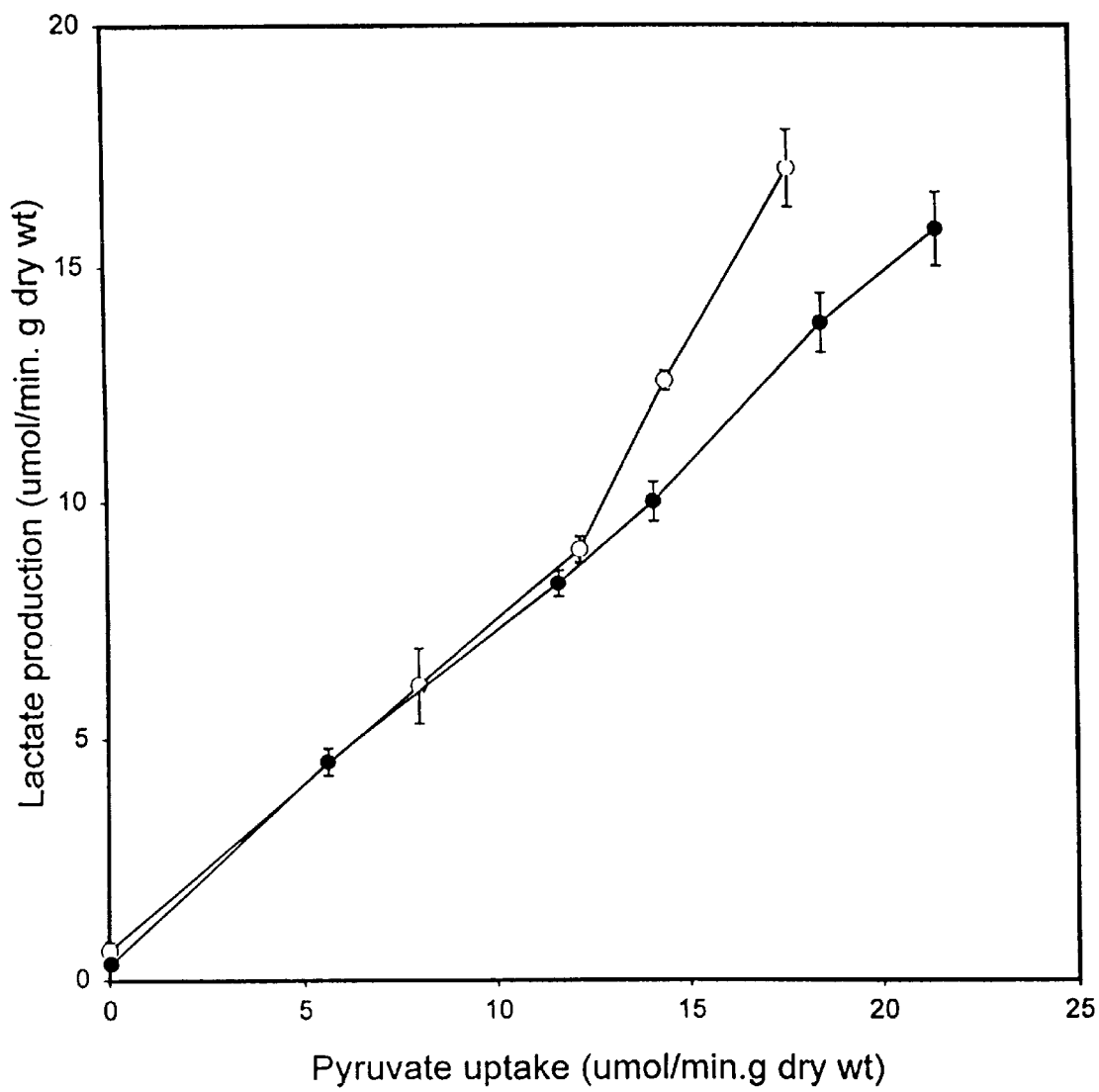
Figure 6:
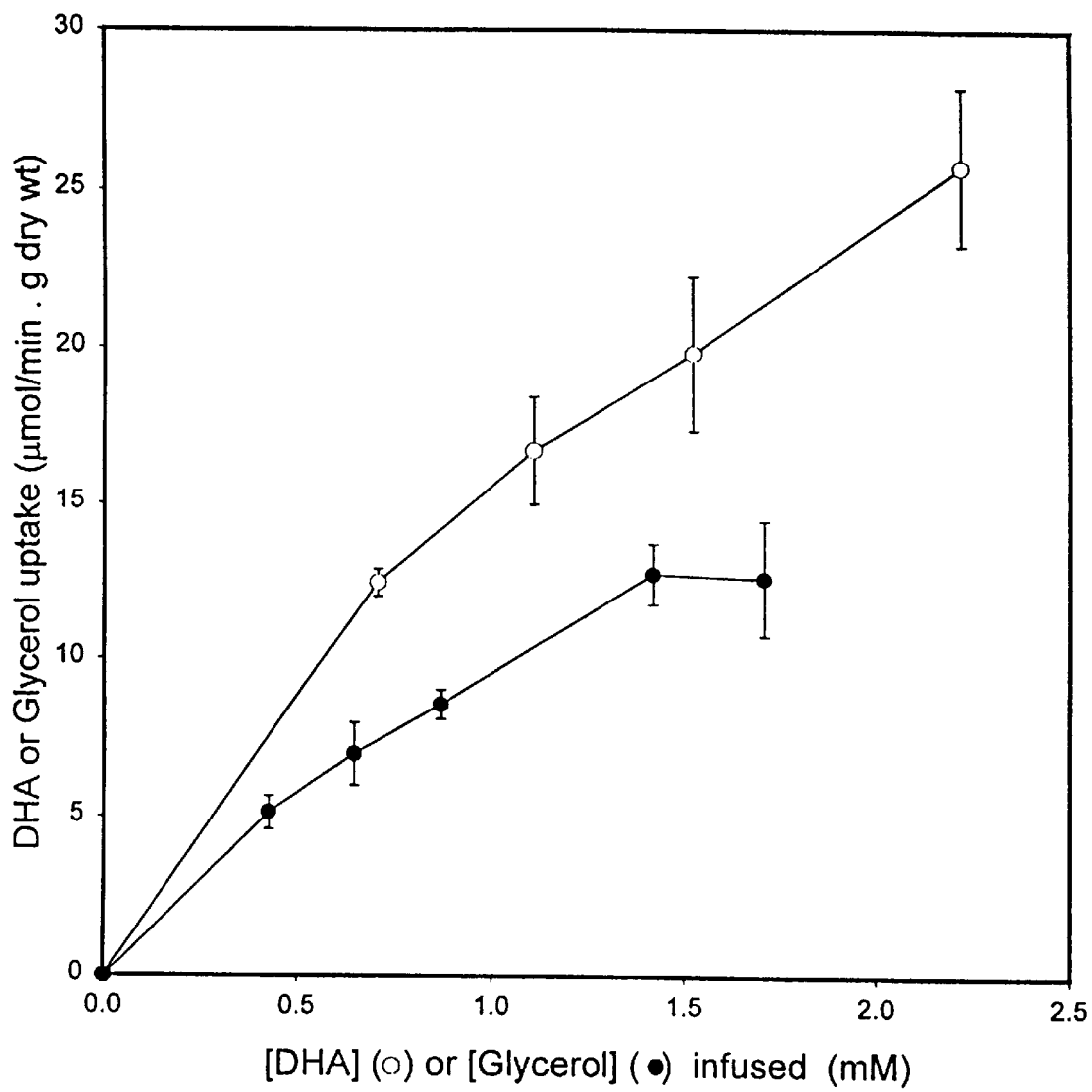

Addition of the components of the pyruvate esters increased ethanol uptake up to 5 fold (FIGS. 3 and 4). As expected, the uptake of ethanol was greater in the presence of DHA than in the presence of glycerol. This clearly shows that DHA contributes to the trapping of reducing equivalents derived from ethanol oxidation. In perfusions with glycerol+pyruvate, correlation between pyruvate uptake and lactate output was linear with a slope of 0.7 (FIG. 5, solid circles). Thus, 70% of the pyruvate taken up was converted to lactate. In perfusions with DHA+pyruvate (FIG. 5, open circles), the correlation had also a slope of 0.7 up to a pyruvate uptake of 13 $\mu$mol/min·g dry wt (corresponding to influent DHA and pyruvate concentrations of 0.7 mM). At higher DHA and pyruvate concentrations, the slope increased to 1.45. However, at the highest DHA and pyruvate concentration used, the ratio (lactate release)/(pyruvate uptake) was 0.96. The fraction of pyruvate uptake not accounted for was presumably converted to glucose and $CO_2$. FIG. 6 shows that the uptake of glycerol and DHA increased with their concentration in the perfusate. As long as the (lactate production)/(pyruvate uptake) ratio was less than 1.0, there was no net conversion of glycerol or DHA to lactate. This occurred only at high DHA concentration.

Figure 7:
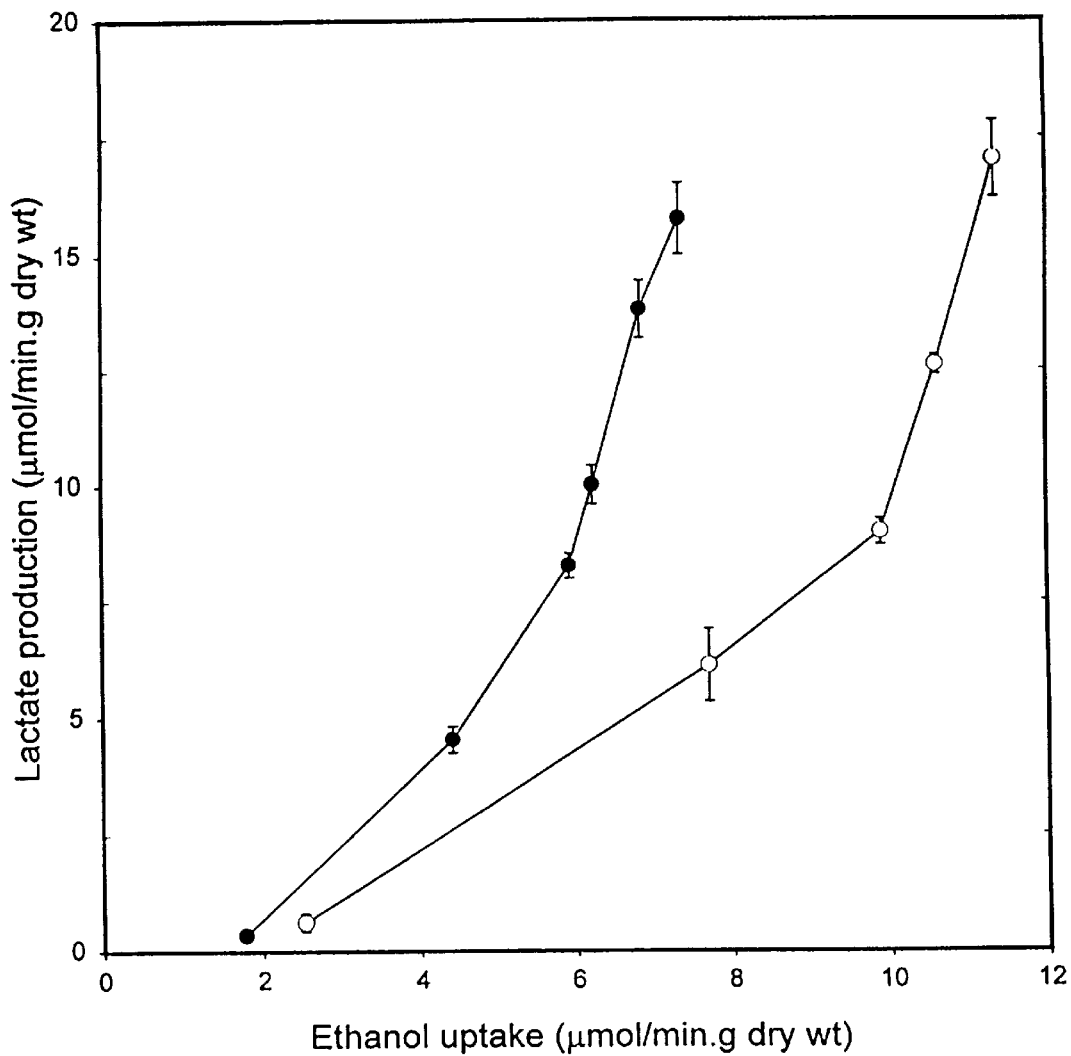

Thus, most of the glycerol and DHA were converted to glucose, glycerides, $CO_2$ or to a combination of these species. FIG. 7 shows the relationship between ethanol uptake and lactate production. Lactate yield was lower when pyruvate was infused with DHA rather than glycerol.

Before the infusion of the components of the pyruvate esters, the effluent [lactate]/[pyruvate] ratio could not be measured with precision, but must have been very high given the presence of ethanol. As the concentrations of the ester components increased from 0.4 to 2.2 mM, the [lactate]/[pyruvate] ratio went down from about 12 to about 2. Thus, essentially all reducing equivalents generated from ethanol were exported as lactate. The oxidized status of the liver $NADH/NAD^+$ system may have allowed oxidation of part of the substrates, including acetate derived from ethanol.

In summary, these experiments confirmed that ethanol oxidation is stimulated by the components of DHA-pyruvate and glycerol-pyruvate. DHA is preferred as it acts not only as an esterifying group for pyruvate but also as a trap for reducing equivalents in its own right.

Therapeutic pyruvate concentration in vivo with DPAG

Figure 8:
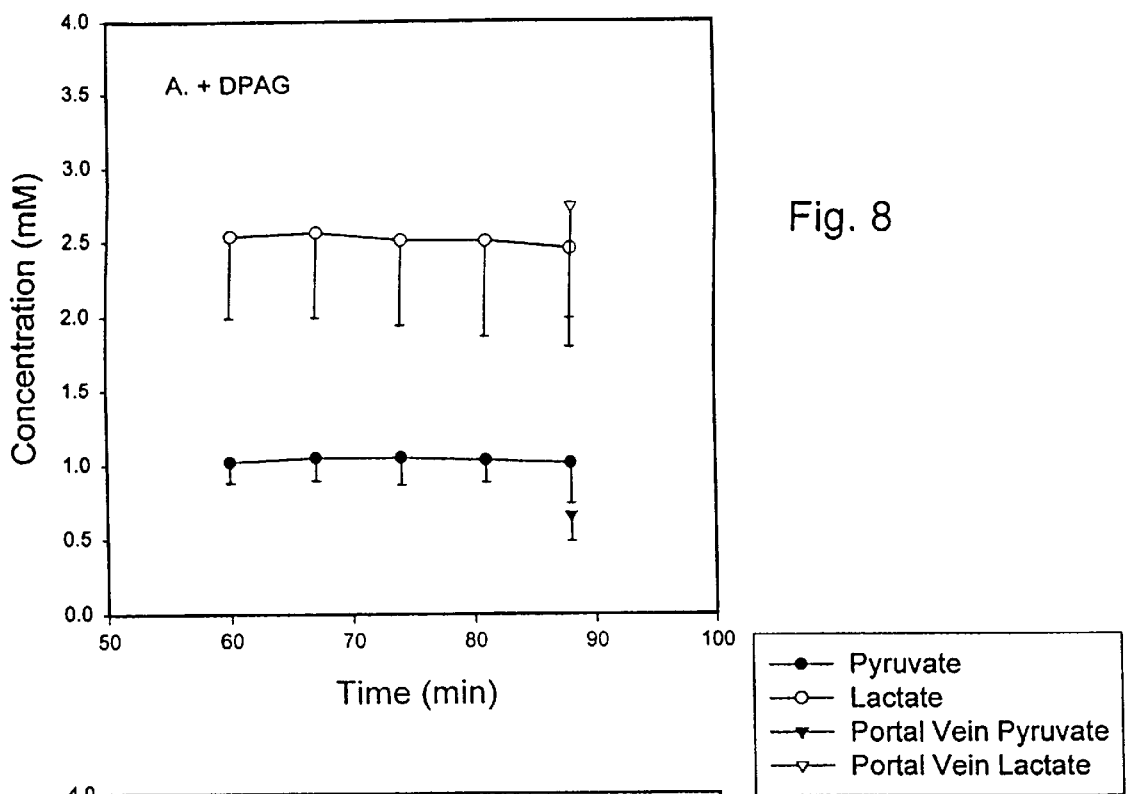
FIGS. 8 and 9 show the results of experiments directed to establish therapeutic pyruvate concentrations in arterial blood.
Figure 9:
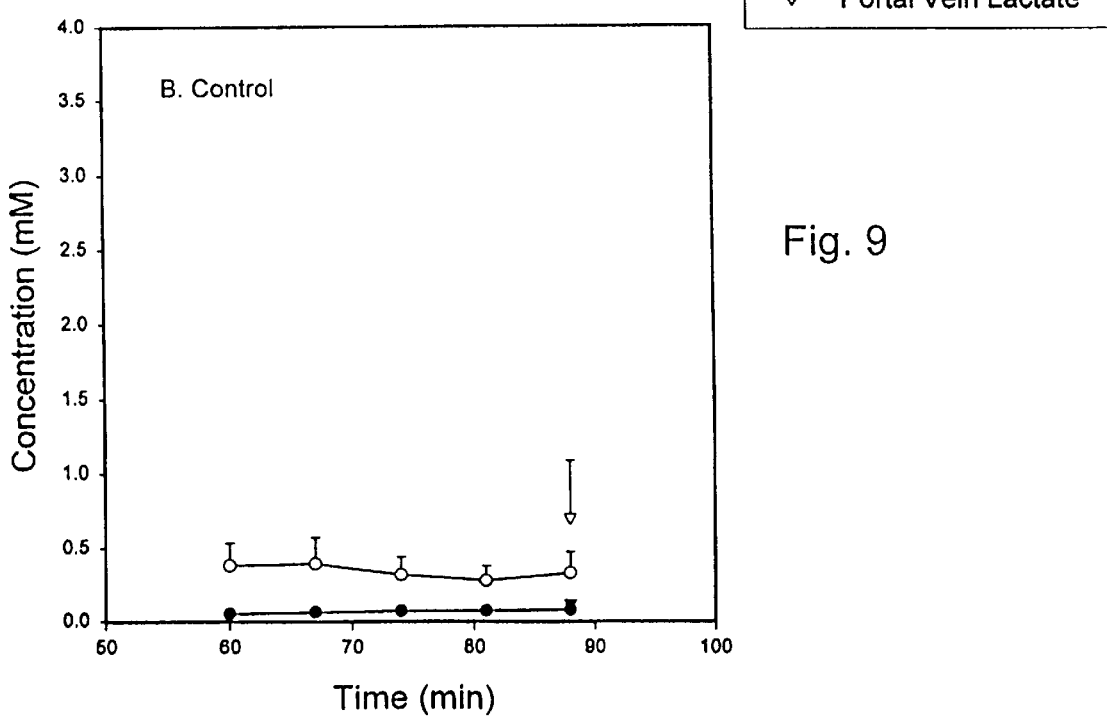

After preparing pure DPAG, experiments were performed to test whether it could be used to impose a therapeutic concentration of 1 mM pyruvate in arterial blood. Overnight-fasted rats, anesthetized with halothane, were infused in the jugular vein with DPAG at 90 $\mu$mol·min$^{-1}$·kg$^{-1}$ for 90 min. This rate corresponds to about 120% of the rats' caloric requirement. Five blood samples (70 $\mu$l) were taken from the carotid artery between 60 and 90 min. The arterial concentrations of pyruvate, lactate, and glycerol were clamped at 1.0, 2.5, and 0.8 mM, respectively. Corresponding portal vein concentrations at 90 min were 0.6, 2.5, and 1.0 mM, respectively. FIGS. 8 and 9 show blood concentrations of metabolites in rats infused with DPAG (panel A) and in control rats infused with saline (panel B).

Control rats show normal arterial concentrations of pyruvate (0.05 mM) and lactate (0.3 to 0.6 mM; normal values for lactate are up to 1.5 mM). In rats infused with DPAG, the arterial concentrations of pyruvate and lactate were clamped at 1.0, and 2.5 mM, respectively. Corresponding portal vein concentrations at 90 min were 0.6 and 2.5 mM, respectively. Arterial glucose remained at 5–6 mM. Final samples of aortic blood showed normal acid-base and electrolyte parameters. Thus, DPAG can be safely used to set up the 1 mM target concentration of pyruvate expected to be beneficial for the treatment of reperfusion injury. Similar data were obtained when PADA was infused to rats. This was achieved without sodium overload and/or acid-base perturbations. Second, the lack of major increases in glucose and lactate concentrations shows that administration of DPAG at 120% of the caloric requirement spares endogenous energy sources, probably including proteins. Third, during peripheral administration of DPAG at 90 $\mu$mol·min$^{-1}$·kg$^{-1}$, portal pyruvate concentration was about ⅔ that which yielded a 3 to 6-fold increase in ethanol uptake by perfused rat livers. A portal pyruvate concentration of 1 mM could be achieved (i) by increasing the peripheral infusion of DPAG to 120 $\mu$mol·min$^{-1}$·kg$^{-1}$, or (ii) by administering DPAG enterally to better target portal vein concentrations.

DPAG can thus be safely used to set up the 1 mM target concentration of arterial pyruvate expected to be beneficial for the treatment of ethanol overdose and reperfusion injury. This was achieved without sodium overload and/or acid-base perturbations. Also, the lack of major increases in glucose and lactate concentrations shows that administration of DPAG at 120% of the caloric requirement spares endogenous energy sources, probably including proteins.

Figure 10:
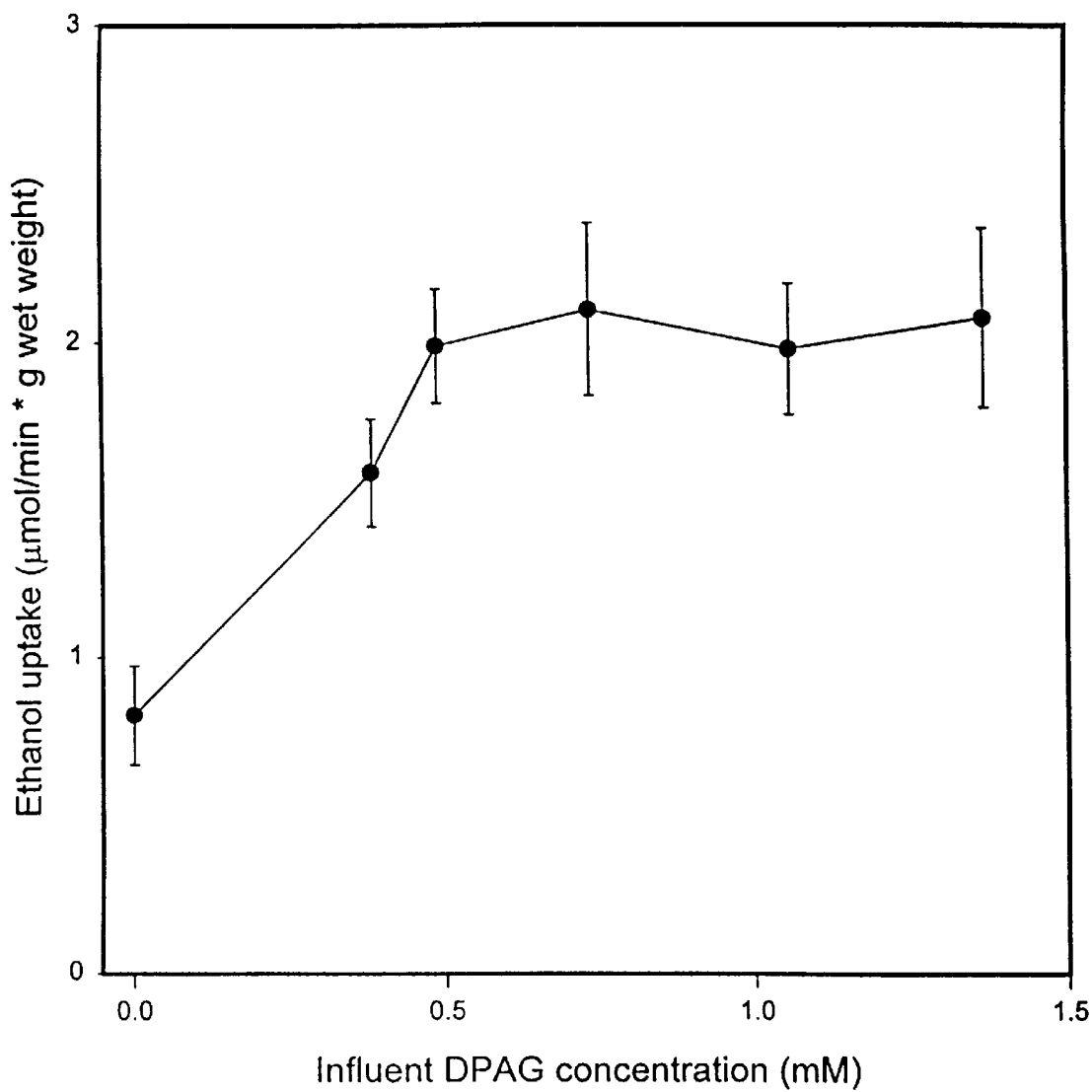
FIG. 10 shows the results of experiments on the effect of DPAG on ethanol uptake.

The effect of DPAG on the rate of ethanol uptake by perfused rat livers was also tested. Livers were perfused with non-recirculating buffer containing 4 mM glucose, 2 mM ethanol and variable concentrations of DPAG (0 to 1.5 mM). FIG. 10 shows that the uptake of ethanol by the liver increases 2.5 fold when DPAG concentration is raised from zero to 0.5 mM. Note that 0.5 mM DPAG corresponds to 1 mM pyruvate after hydrolysis. Thus, to accelerate ethanol oxidation in vivo, the rate of DPAG administration should be adjusted to achieve a 1 mM concentration of free pyruvate in the portal vein. When DPAG was infused to live rats at 90 $\mu$mol·min$^{-1}$·kg$^{-1}$, the portal vein concentration of pyruvate was 0.6 mM. A portal pyruvate concentration of 1 mM could be achieved in vivo (i) by increasing the peripheral infusion of DPAG to 120 $\mu$mol·min$^{-1}$·kg$^{-1}$, or (ii) by administering DPAG enterally to better target portal vein concentrations.

Accordingly, DPAG and PADA are effective in the treatment of alcoholic coma to prevent complications such as brain damage, hypothermia, respiratory depression, and pulmonary infection and in the oral intake of the esters in conjunction with ingestions of alcoholic beverages, to accelerate ethanol oxidation and restore the capacity to drive a vehicle or operate machinery.

Synthesis of DPAG

DPAG was prepared by esterification of 1-acetyl-glycerol (1-monoacetin) with pyruvyl chloride. To a 250 ml three-neck flask fitted with a thermometer, a mechanical stirrer, a 25 ml dropping funnel, and flushed with dry nitrogen, one adds 5.0 g of anhydrous monoacetin (dried for 2 days under vacuum), 0.0 ml of anhydrous pyridine, and 100 ml of anhydrous benzene. The flask is cooled below 10° C. with an ice+salt slurry. Freshly distilled pyruvyl chloride (6.0 ml, 1 equivalent) is added dropwise over 15 min, while maintaining the temperature below 10° C. Then, the reaction mixture (showing a white precipitate of pyridinium chloride) is stirred for 1 hr at room temperature. The reaction mixture is filtered, to remove the pyridinium salt, and concentrated at 30° C. on a rotavapor under high vacuum. The crude yellow product is dissolved in 50 ml of chloroform, washed once with 10 ml of HCl 1N, and stirred with 4g of Amberlyst-15 for 4 hr. The solvent is evaporated on a rotavapor under high vacuum at 30° C. maximum. The yield of DPAG (light yellow oil) is 9.6 g (94%).

The formula of DPAG was verified by (i) NMR $^1$H and $^{13}$C, (ii) infrared spectra, (iii) enzymatic assay of the components of DPAG after hydrolysis, and (iv) HPLC before and after hydrolysis.

NMR $^1$H (200 MHz Varian), solvent CDCl$_3$, reference TMS ($\delta$ in ppm): 5.30 (m, 1H, CH); 4.50–4.00 (m, 4H, CH$_2$O); 2.40 (s, 6H, CH$_3$COCO); 2.00 (s, 3H, CH$_3$CO)

NMR $^1$H in agreement with the formula and the theoretical NMR spectra software ACD/LABS DEMO.

NMR $^{13}$C (200 MHz Varian), solvent CDCl$_3$, reference TMS ($\delta$ in ppm): 188.9, 188.7 (2C, carbonyls); 170.2 (1C, acetyl); 157.8, 157.9 (2C, pyruvyl); 68.9 (1C, CH); 61.5, 59.4 (2C, CH$_2$O); 24.6 (2C,CH$_3$); 18.4 (1C, CH$_3$) in agreement with the formula and the theoretical NMR spectra software ACD/LABS DEMO.

IR (cm$^{-1}$, CCl$_4$): 3537 (OH bonds from hydrated C=O), 2984; 1756, 1751, 1740, 1736, 1729 (C=O); 1383, 1231.

The NMR and IR spectra show that two molecules of water are fixed on carbonyl groups to form stable hydrated keto esters.

Incubation of DPAG with pig liver esterase liberates the components of the ester which were determined by enzymatic assays, thus confirming the formula of DPAG.

Synthesis of PDAG

PDAG was prepared in 81% yield by reacting diacetyl-glycerol with pyruvyl chloride, using the above procedure.

The formula of PDAG was verified by (i) NMR $^1$H and $^{13}$C, (ii) infrared spectra, (iii) enzymatic assay of the components of DPAG after hydrolysis, and (iv) HPLC before and after hydrolysis.

NMR $^1$H (200 MHz Varian); solvent: CDCl$_3$, reference TMS ($\delta$ in ppm): 5.28 (m, 1H, CH); 4.38–4.14 (m, 4H, CH$_2$O); 2.41 (s, 3H, CH$_3$COCO); 2.01 (s, 6H, CH$_3$CO). NMR $^1$H in agreement with the formula. NMR $^{13}$C (200 MHz Varian), solvent: CDCl$_3$, reference TMS ($\delta$ in ppm): 190.9 (1C, carbonyl); 170.4 (2C, acetyl); 159.8 (1C, pyruvyl); 71.5 (1C, CH acetyl); 68.6 (1C, CH pyruvyl); 61.9, 61.8 (2C, CH$_2$O); 24.7 (1C, CH$_3$ pyruvyl); 20.6 (2C, CH$_3$ acetyl) in agreement with the formula. IR (cm$^{-1}$, CCl$_4$): 3593 (OH bond, from hydrated C=O), 2973, 1762 (C=O bond), 1752 (C=O bond), 1744 (C=O bond), 1736 (C=Obond), 1374, 1242.

The NMR and IR spectra show that on a small fraction of the molecules, one molecule of water is fixed on a carbonyl group to form a stable hydrated keto ester.

Synthesis of PADA

PADA was prepared in 95% yield by esterification of dihydroxyacetone monoacetyl with pyruvyl chloride, as above.

TLC on silica (developed with chloroform/methanol/hexane 12/1/1 and revealed with iodine) showed one spot corresponding to PADA (Rf 0.45–0.50), and no dihydroxyacetone, dihydroxyacetone monoacetate, or diacetate.

The formula of PADA was verified by (i) NMR $^1$H and $^{13}$C, (ii) infrared spectra, (iii) enzymatic assay of the components of PADA after hydrolysis, and (iv) HPLC before and after hydrolysis.

NMR $^1$H (200 MHz Varian), solvent CDCl$_3$, reference TMS ($\delta$ in ppm): PADA (keto form):4.94 (s, 2H, $CH_2OCOCO$); 4.74 (s, 2H, $CH_2OCO$); 2.49 (s, 3H, $CH_3COCO$); 2.08(s, 3H, $CH_3CO$). NMR $^{13}C$ (200 MHz Varian), solvent $CDCl_3$, reference TMS (δ in ppm): PADA (keto form):198.0 (1C, keto of DHA); 192.9 (1C, keto of pyruvyl); 170.1 (1C, acetyl); 159.1 (1C, pyruvyl); 67.3, 66.3 (2C, $CH_2O$); 26.7 (1C, $CH_3$, pyruvyl); 20.3 (1C, $CH_3$ acetyl). Spectra in agreement with the formula. Enzymatic assay of pyruvate after hydrolysis was in agreement with the formula.

Pyruvate and the Krebs Cycle

As is well recognized, several oxidation steps in the Krebs cycle involve dicarboxylic and tricarboxylic acids. However, it is understood that a certain malfunction of this cycle can occur via leakage of dicarboxylic and tricarboxylic acids (cataplerosis). It is believed the pyruvate delivered in accord with this invention can restore Krebs cycle effectiveness by "refilling" the pools of dicarboxylic and tricarboxylic acids (anaplerosis).

Dermatological uses of Pyruvate

Dermatologic applications of the above described pyruvate esters and thioesters have been identified. As described more fully herein below, the novel pyruvates can be used as active agents or as preservatives in topical and oral dermatologic applications.

Particularly, the compounds are suitable for stabilization of all topical preparations or oral preparations to prevent oxidative damage to the ingredients in the formulation of, for instance, sunscreen chemicals and their stabilizers, antioxidants and the associated preservatives, cosmetic antioxidants, bioactives, or other formulation purposes; oral agents in suspension in which the suspension needs or could be enhanced by a safe anti-oxidant.

Similarly, the compounds can be added to the composition of tanning creams where the tanning effect of the dihydroxyacetone (DHA) moiety will be complemented by the antioxidant action of the pyruvate and thiol moieties of the pyruvate esters and thioesters.

The result is believed to be protection of the skin against oxidative injury caused by a number of conditions including, but not limited to environmental stress from ultraviolet radiation (including prevention and treatment of sunburns) and routine suberythemogenic light exposure, and pollutants (including tobacco smoke), endogenous stress resulting from diseases (cancer, infections, inflammatory conditions, etc.), and diaper dermatitis-dermatological wound healing composition.

The compounds will also prevent, reduce and heal physical and chemical damage resulting from contact with harmful chemicals, radiation therapy damage including chemotherapy complication, laser exposure, laser surgery, electrochemical destruction, all skin peels, whether via chemical destruction (i.e., phenol, glycolic acids, alpha hydroxy acids, or other acids) or physical destruction (liquid nitrogen, laser light, other electromagnetic radiation or electro destructive, photodynamic therapies, etc.) can also be reduced via the present pyruvate compounds. In fact, the compound should be suitable to reduce general aging (chronologic aging), structural changes and wrinkling (photoaging, tobacco aging) of the skin.

In each instance, the pyruvate esters and thioesters of this invention are particularly advantageous because they are soluble in typical ointments and creams and less damaging to the skin than prior pyruvate compounds. Examples of suitable systems for delivery include ointments, creams, emulsions, lotions, mousses, gels, sprays, microencapsulated powders, solutions, dispersions, patches, bandages or any other form known to those skilled in the art.

Pyruvate esters, as an antioxidant, would be expected to attenuate inflammation, damage and aging of the skin through oxidative injury. Because pyruvate esters blocks UW-induced inflammation in human skin, one can reasonably predict that the esters will act on the inflammatory mechanisms that create inflammation in the skin after UV radiation injury, and which are shared by many other skin diseases. These include, but are not limited to, soluble mediator release (eicosanoids, histamine, mast cell products), reactive oxygen species mediated skin damage (both as a direct effect of photons reacting with skin cellular and structural elements and as a result of cellular ROS generated secondarily to the injury), DNA damage, cellular reactivity to UV-induced products (direct photoproducts, mediators, chromophores, DNA excision products, products of oxidation), cytokine release and action, skin reconstruction, bone marrow derived cell activation, infiltration of leukocytes and their activation, vascular endothelial cell activation, adhesion molecule function and expression, fibroblast function, complement activation, fibronectin modification, immune function alteration.

In addition, it is expected that the compounds will assist with all skin cell activations that occur in other skin conditions that result in generation of reactive oxygen species or nitric oxide; most inflammatory reactions in the skin are associated with, and may be critically dependent upon, ROS or NO generation during the evolving pathogenic events in time and microanatomic location in the skin. In short, the pyruvate esters, as a safe and effective topical antioxidant, would be useful as both a protecting ingredient and for promoting the health and resistance of skin against aging and injury. Similarly, it is believed that skin cell damage may be increased by the decrease of ROS by leukocytes which travel to the intially injured skin. The pyruvate which are believed to block the leukocytes and/or their ROS generation can help to reduce this effect.

The following list of dermatological applications derives from the above understanding:

Prevention and treatment of inflammation in the skin.

Prevention of damage (including sunburn) from natural solar radiation or tanning beds or industrial/occupational exposure UV.

Prevention of skin cancer, either via prevention of tumor promoting inflammation, or via prevention of oxidant mediated mutations in DNA.

Prevention of photoaging, such as loss of elasticity, immune function, development of solar lentigos (liver spots), actinic keratoses, dryness of the skin, wrinkling, sallow color.

Prevention of skin injury and reduction of inflammation from chemicals, pesticides, wind or other environmental agents.

Prevention of skin aging.

Compensation for aging skin diminishment of ROS defense and the sequelae of such.

Improve skin function in the face of repeated exposure to UV radiation and chemicals.

Prevent skin aging processes attributable to ROS damage, including dryness, poor wound repair, poor immune function, easy bruisability, loss of elasticity, wrinkling, sallow color.

Prevention and treatment of UV-induced immunosuppression and immune alteration of the skin.

Protection against injurious substances or environmental hazards which damage the skin such as carcinogens with direct or indirect oxidant effects, cold injury and frostbite, thermal and chemical burns, chemical irritants.

Treatment of inflammatory skin diseases.

Treatment of autoimmune diseases with activated leukocytes such as, but not limited to atopic dermatitis, xerotic eczema (dry skin), psoriasis, dermatitis herpetiformis, alopecia areata, granuloma annulare, sarcoid lupus erythematosis, lichen planus, scleroderma, graft vs. host disease.

Treatment of other inflammatory diseases with activated leukocytes such as, but not limited to, contact dermatitis, drug reactions, erythema craquile, spongiotic dermatitis, lichen simplex chronicus, urticaria, toxic epidermal necrolysis, Stevens Johnson Syndrome, erythema multiforme.

Treatment of other inflammatory skin conditions, such as, but not limited to, vasculitis, pyoderma gangrenosum, skin wounds, skin ulcers, keloids, scarring from wounding and wound repair.

Prevention of exacerbation or relapse of inflammatory skin diseases that may be in partial or complete remission, such as, but not limited to, atopic dermatitis (eczema), psoriasis, xerotic eczemas, stasis dermatitis, psoriasis, lupus erythematosis.

Reduction and prevention of vasculitis from all causes or no known underlying cause.

Reduction and prevention of skin ulcers from all causes or no known underlying cause.

Reduction of damage from melanomas and prevention of pigmentation response such as skin hyperpigmentation and early changing melanocytes.

It is believed that internal administration of compounds for prevention of photoinjury, thermal, or chemical injury to areas not able to be protected by topical administration of material, for instance scalp, ears, lips, periocular skin, eyelids, conjunctivae, cornea, scleral conjunctivae, lens, vitreous, and retina and even the exposed skin diseases and conditions are cetainly feasible. In any event, it is believed that 1–30 ppm pyruvate may adequately achieve many of the above treatments. However, levels of about 0.01 to 1.0% and above are preferred.

Evaluations of Dermatological Applications

1) Pyruvate ester compounded in ethylene glycol/aquaphor per separate notes at 0.01%, 0.03%, 0.1%, 0.3%, 1.0%, 3.0%

2) Stored at 4° C. in capped syringes

3) Twice daily applications, beginning with 0.01% and observing the test site for irritation for 8–12 hours before proceeding to the next concentration 4) 0.8 cc of each conc. was applied to the volar forearm at one of a set of premarked 2 cm² areas corresponding to each conc.

5) After no irritation was observed for the 0–0.1% preparations, the test sites were administered natural solar radiation (4 hr. post AM test material application)

6) Between 11:00 AM–11:25 AM, the volar forearm was exposed to natural solar radiation, and 4 hr. later another 0.8 cc of test materials were applied to the appropriate sites 6) 7 hours later the sites were graded by subjective assessment and Minolta chromameter.

Three chromameter measurements of three flashes each were taken from each site.

Results:

1) Irritation testing:

| | Day | Redness | Surface | Sensation | Odor |
|---|---|---|---|---|---|
| Aquaphor | 0 | none | sl. xerosis | none | none |
| | 1 | none | smooth | none | none |
| | 2 | trace | smooth | none | none |
| 0.01% | 0 | none | sl. xerosis | none | none |
| | 1 | none | smooth | none | none |
| | 2 | faint trace | smooth | none | none |
| 0.03% | 0 | none | sl. xerosis | none | none |
| | 1 | none | smooth | none | none |
| | 2 | none | smooth | none | none |
| 0.10% | 0 | none | sl. xerosis | none | none |
| | 1 | none | smooth | none | none |
| | 2 | none | smooth | none | none |
| 0.30% | 0 | none | sl. xerosis | none | none |
| | 1 | none | smooth | none | none |
| | 2 | | | | |
| 1.00% | 0 | none | sl. xerosis | none | slight, pungent |
| | 1 | none | smooth | none | none |

Redness: 7 hours post NSR

| Dry Adjacent | Pyruvate Conc. | Chromameter Redness | | Mean | SEM | Redness: Subj. |
|---|---|---|---|---|---|---|
| Skin | 0 | 9.74 | | 9.74 | | trace |
| Aquaphor | 0.00 | 10.17 | Pyruvate | | | trace |
| | 0.00 | 9.42 | Conc | redness | | |
| | 0.00 | 10.50 | 0.00 | 10.03 | 0.32 | |
| mg % in | 0.01 | 8.72 | | | | faint-trace |
| Aquaphor | 0.01 | 8.48 | | | | |
| | 0.01 | 8.78 | 0.01 | 8.66 | 0.09 | |
| | 0.03 | 7.19 | | | | none |
| | 0.03 | 6.81 | | | | |
| | 0.03 | 6.20 | 0.03 | 6.73 | 0.29 | |
| | 0.10 | 6.51 | | | | none |
| | 0.10 | 6.32 | | | | |
| | 0.10 | 6.41 | 0.10 | 6.41 | 0.05 | |

Conclusion: Pyruvate ester in aquaphor is non-irritating and can block experimentally induced skin inflammation in human skin Pigmentation 48 hours post NSR

| | Pyruvate Ester Conc. | Chromameter pigmentation (1/L) | | | |
|---|---|---|---|---|---|
| | 0 | 0.01523 | Pyruvate | | |
| Aquaphor | 0.00 | | Conc. | pigmentation (1/L) | |
| | 0.00 | | 0.00 | 0.01523 | |
| mg % in | 0.01 | 0.01500 | | | |
| Aquaphor | 0.01 | | 0.01 | 0.01500 | |
| | 0.03 | | | | |
| | 0.03 | 0.01476 | | | |
| | 0.03 | | 0.03 | 0.01476 | |
| | 0.10 | 0.01428 | | | |
| | 0.10 | | | | |
| | 0.10 | | 0.10 | 0.1428 | |

-continued

| | Pyruvate Ester Conc. | Chromameter pigmentation (1/L) |
|---|---|---|
| dry, unexposed skin | | 0.01334 |

Conclusion: Pyruvate ester prevented melanocytic response to UV as measured by tanning induction (reciprocal of lightness value by chromameter)

Redness: 48 hours post NSR

| Dry Adjacent | Pyruvate Ester Conc. | Chromameter Redness | | | Redness: Subj. |
|---|---|---|---|---|---|
| Skin | 0 | 5.33 | | 5.33 | trace |
| Aquaphor | 0.00 | 9.40 | Pyruvate Conc | redness | trace |
| | 0.00 | | 0.00 | 9.40 | |
| | 0.00 | | | | |
| mg % in | 0.01 | 8.31 | | | faint-trace |
| Aquaphor | 0.01 | | | | |
| | 0.01 | | 0.01 | 8.31 | |
| | 0.03 | 6.28 | | | none |
| | 0.03 | | 0.03 | 6.28 | |
| | 0.10 | 6.94 | | | none |
| | 0.10 | | | | |
| | 0.10 | | 0.10 | 6.94 | |

Redness: 48 hours post NSR

| Dry Adjacent | Pyruvate Ester Conc. | Chromameter Redness | a* | | |
|---|---|---|---|---|---|
| Skin | 0 | 5.33 | | | 5.33 |
| Aquaphor | 0.00 | 9.40 | 4.07 | Pyruvate Conc. | redness |
| | 0.00 | | | 0.00 | 9.40 |
| | 0.00 | | | | |
| mg % in | 0.01 | 8.31 | 2.98 | | |
| Aquaphor | 0.01 | | | | |
| | 0.01 | | | 0.01 | 8.31 |
| | 0.03 | 6.28 | 0.95 | | |
| | 0.03 | | | | |
| | 0.03 | | | 0.03 | 6.28 |
| | 0.10 | 6.94 | 1.61 | | |
| | 0.10 | | | | |
| | 0.10 | | | 0.10 | 6.94 | a* = Change in Redness from Baseline of Dry Adjacent Skin

These results are further represented in the Tables attached as FIGS. 12–16.

Treatment for Diabetic Ketosis

Under normal conditions, glucose and long-chain fatty acids (FA) are the major energy fuels for most tissues. Ketone bodies (KB), i.e., acetoacetate (AcAc) and R-β-hydroxybutyrate (R-BHB, also called D-BHB) are formed from the partial oxidation of FA in liver. These strong acids are totally ionized at physiological pH. KB are important fuels in fasting, strenous exercise, postexercise recovery, etc (1,2). They accumulate in starvation and diabetic ketoacidosis (DKA).

With respect to this invention, it is believed in theory, but not a theory to which Applicants intend their invention to be limited that ketogenesis is fueled by FA released by adipose tissue lipolysis. The uptake of FA by the liver is directly proportional to their plasma concentration. In liver cytosol, FA are activated to acyl-CoAs which are either incorporated into lipids, or channeled to the mitochondria for oxidation. Transfer of acyl-CoAs to the mitochondria occurs via the carnitine palmitoyl transferases I and II (CPT I and II), with transient conversion to long-chain acyl-carnitines. The activity of CPT I, a major regulator of the entry of LC-acyl-CoAs into mitochondria, is inhibited by malonyl-CoA, an intermediate of fatty acid synthesis (see below). Once in liver mitochondria, acyl-CoAs undergo β-oxidation to acetyl-CoA. The three main fates of mitochondrial acetyl-CoA are (i) oxidation to $CO_2$ via citrate in the citric acid cycle (CAC), (ii) transfer to the cytosol via citrate and ATP-citrate lyase, and (iii) conversion to ketone bodies Ketogenesis is regulated at three levels: supply of FA to the liver, β-oxidation of FA in liver, and energy status of the liver. First, the release of FA from adipose tissue is under hormonal control. It is stimulated by catecholamines and glucagon via hormone-sensitive lipase. It is inhibited by insulin. Second, in liver, the β-oxidation of FA is under nutritional and hormonal control. It is activated by starvation, diabetes, and high-fat diet and inhibited by high-carbohydrate diet. In addition, FA oxidation is inhibited by malonyl-CoA, an intermediate of FA synthesis. This provides a reciprocal control of FA synthesis and oxidation. Third, ketogenesis represents a spillover of carbon derived from FA β-oxidation which cannot be oxidized in the CAC. Since CAC activity is directly linked to ATP turnover, and since the flux through β-oxidation often exceeds the CAC flux, excess p-oxidation carbon is exported as ketone bodies. This explains why hypermetabolic states (burn or crush injuries) that result in increased liver ATP turnover, are associated with low plasma ketone body concentrations in spite of the stimulation of lipolysis by stress hormones.

Although ketogenesis can be greatly activated by dietary and hormonal manipulations, its absolute maximal rate is set by the $O_2$ uptake of the liver in a given metabolic situation. This rate can be calculated by assuming that all the $O_2$ uptake of the liver is used only to oxidize reducing equivalents formed during the conversion of FA to R-BHB.

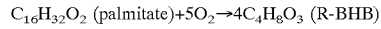

$C_{16}H_{32}O_2$ (palmitate)+$5O_2 \rightarrow 4C_4H_8O_3$ (R-BHB)

For example, consider a 20 kg dog with a 500 g liver that takes up $O_2$ at 2 $\mu$mol·min$^{-1}$·(g liver)$^{-1}$ or 1 mmol·min$^{-1}$, which corresponds to a R-BHB production of 0.8 mmol·min$^{-1}$, or 1.15 mol·day$^{-1}$. This is clearly an unrealistic maximal rate since, to achieve it, no $O_2$ would be used for any other metabolic process in liver. However, this maximal rate is useful to discuss mechanisms of DKA.

R-BHB and AcAc represent a water-soluble form of FA which are transported from the liver to peripheral tissues. There, KB are converted to acetyl-CoA by mitochondrial 3-oxoacid CoA transferase (OAT) and AcAc—CoA thiolase:

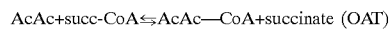

AcAc+succ-CoA⇌AcAc—CoA+succinate (OAT)

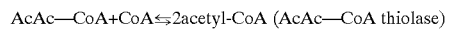

AcAc—CoA+CoA⇌2acetyl-CoA (AcAc—CoA thiolase)

In peripheral tissues, acetyl-CoA derived from KB has two main fates, (i) oxidation to $CO_2$ via the CAC, and (ii) transfer to the cytosol via citrate and ATP-citrate lyase (in lipogenic organs: adipose tissue, developing brain, lactating mammary gland).

In a given metabolic condition, the rate of KB uptake by peripheral tissues is roughly proportional to their plasma concentration over a wide dynamic range (1–4). When entering a given tissue, KB compete with other fuels (FA and glucose) for the production of acetyl-CoA. This competition is influenced by the OAT activity of each tissue, the concentration of competing fuels, and the rate of acetyl-CoA production from competing fuels Consider the 20 kg dog. Its daily caloric requirement is $110 \cdot 20^{0.75} = 1040$ kcal/day. If all this caloric requirement were met by R-BHB oxidation (4.7 kcal/g), the dog would oxidize 221 g or 2.1 mol/day. This is about twice the theoretical maximal rate of ketogenesis. There is evidence that the capacity of peripheral tissues to utilize KB is not far from the theoretical maximum. For example, dogs were infused with 1,3-butanediol diacetoacetate (4), a sodium-free precursor of KB (5), at 90% of their caloric requirement. This corresponds to a rate of R-BHB infusion of 1.8 mol/day. The plasma concentration ot total KB plateaued at 3 mM, reflecting metabolism of all the infused compound. Also, in pigs infused with 1,3-butanediol diacetoacetate at 30% of caloric requirement, the steady state total KB concentration plateaued at only 0.5 mM. This is remarkable given that pigs are deficient in liver mitochondria HMG-CoA synthase, and have thus a very low capacity to make KB. Thus, in normal animals, peripheral tissues including the brain take up avidly KB when their plasma concentration is raised.

One of the main characteristics of decompensated insulin-dependent diabetes, in addition to hyperglycemia, hypokalemia, and dehydration, is ketoacidosis (up to 20 mM), resulting in life-threatening perturbations of acid/base status. DKA results from an imbalance between KB production and utilization. Reviews from the literature emphasize the concept that DKA results mostly from hyperproduction of KB. Although a decrease in the capacity of peripheral tissues to utilize KB is mentioned. Strategies for decreasing ketosis are solely aimed at (i) inhibiting adipose tissue lipolysis (insulin), and (ii) inhibiting the conversion of FA to KB in liver. To the best of our review of the literature, there are no strategies for accelerating KB utilization in peripheral tissues. Based on the above, we think that underutilization of KB by peripheral tissues is a key component of the development of DKA.

To avoid the sodium load, we synthesized esters of pyruvate and glycerol or dihydroxyacetone (DHA). Glycerol and DHA are the only esterifying compounds which can be administered in large amounts. Glycerol is a physiological substrate which is released by lipolysis mostly from adipose tissue. About 25% of glycerol production is taken up by the liver, 25% by the kidneys, and 50% by peripheral tissues. Although DHA is not a physiological substrate, it is metabolized by glycerol kinase to DHA-phosphate, which is also a product of glycerol metabolism.

Prediabetic male BB rats were purchased from the University of Massachussetts Breeding Center. They were treated with insulin (PZI 40 U/mL, Anpro Pharmaceutical), mean of 2.1 U for rats weighing between 250–300 g) as soon as they became hyperglycemic. They were used after at least three weeks of clinical stability and steady weight growth. Under general anesthesia, permanent catheters were inserted in a carotid artery and the controlateral external jugular vein. Then, the rats were deprived of insulin for two days. This resulted in hyperketonemia (9–12 mM), hyperglycemia (22.6±1.8 mM, n=18), and loss of weight (39 g over 2 days). The rats were then treated with one of four protocols:
(i) saline infusion (0.267 ml/min. kg for 2 h then 0.134 ml/min kg for 2 h); (ii) saline infusion+0.75 U of insulin intravenously (at 0 and 2 h); (iii) DPAG (90 µmol·min⁻¹kg⁻¹, corresponding to 120% of caloric requirement of a normal rat of similar weight) in saline infusion; and (iv) DPAG in saline infusion+0.75 U of insulin intravenously (at 0 and 2 h).

Figure 17:
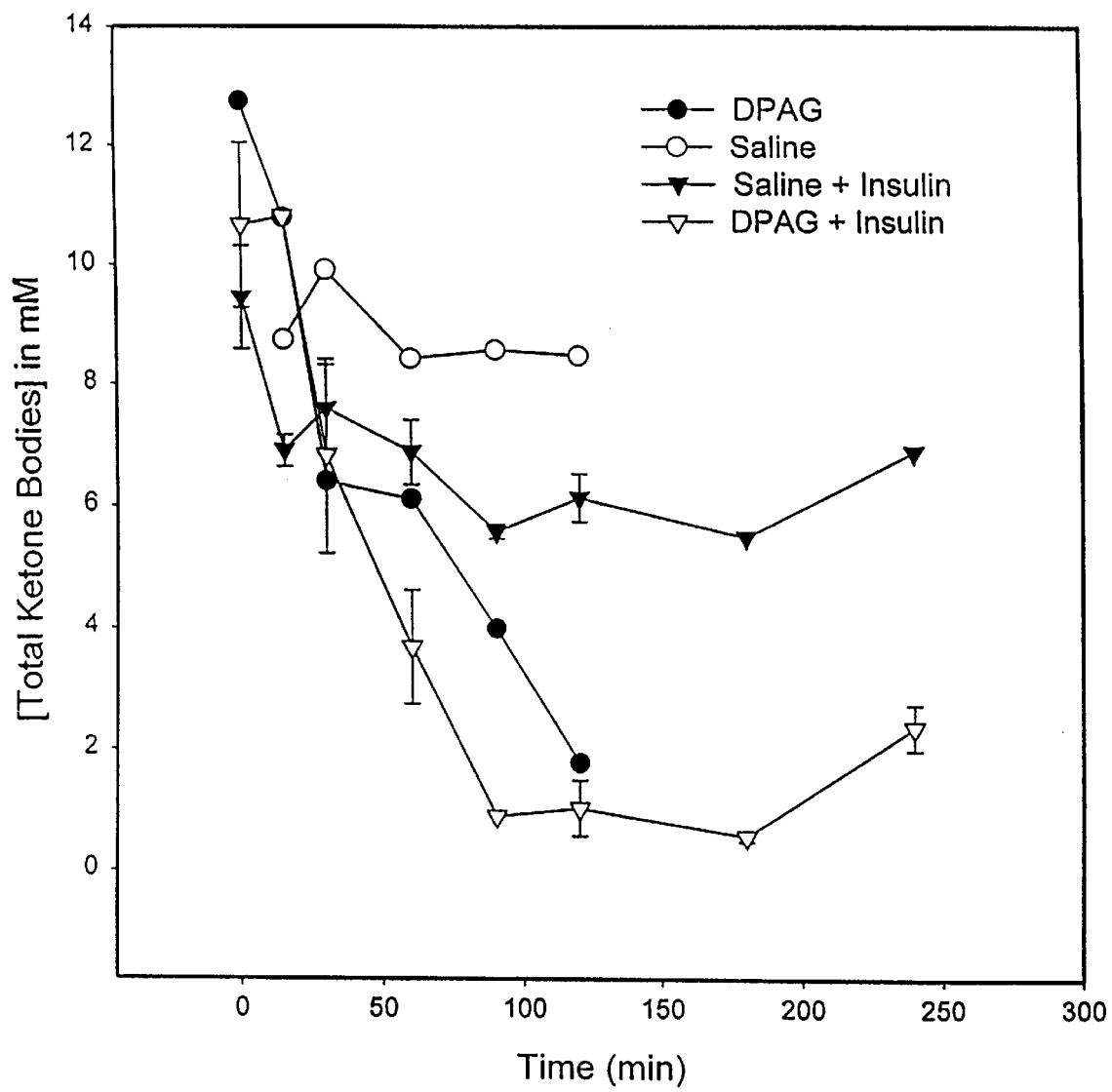
FIG. 17 shows DPAG effect on ketone bodies in ketoacidotic diabetic rats.
Figure 18:
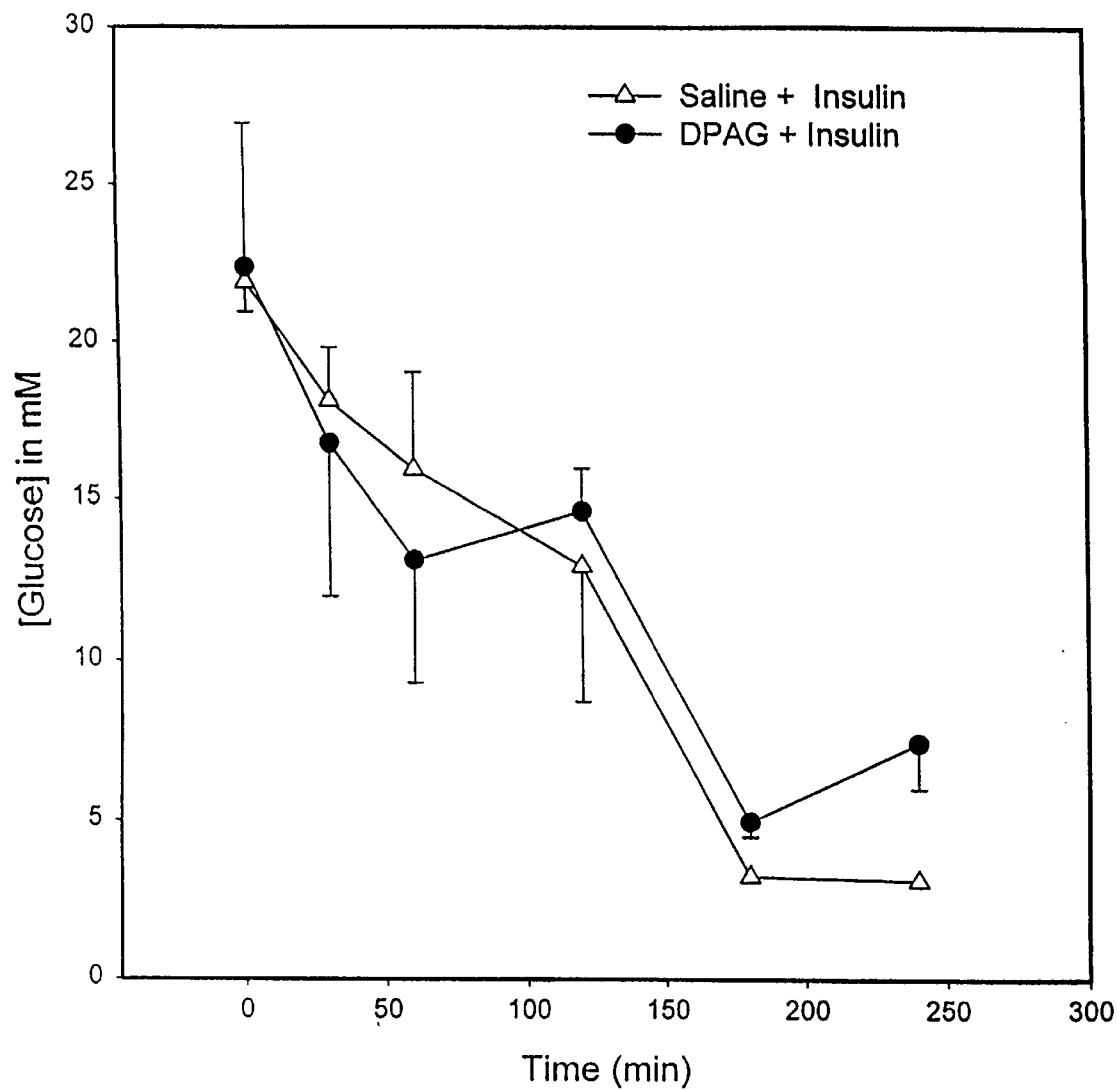
FIG. 18 shows DPAG effect on blood glucose in ketoacidotic diabetic rats.

FIG. 17 shows that, with DPAG treatment, total KB concentration decreased by 90% in 2 hr, much faster than with insulin treatment (30%). When DPAG and insulin were administered together, their effect on ketosis was partly additive (FIG. 17). Also, DPAG did not blunt the decrease in glucose concentration induced by insulin (FIG. 18). The data show that massive doses of DPAG are well tolerated by compromised BB rats in diabetic ketoacidosis. Thus, we hypothesize that DPAG could become part of the treatment of DKA. DPAG may decrease ketosis by (i) inhibition of lipolysis in adipose tissue, (ii) inhibition of the conversion of FA to KB in liver, and (iii) restoration of KB oxidation in peripheral tissues.

Pyruvate esters are not meant to replace the usual treatment of DKA by rehydration and insulin. They are meant to reinforce the usual treatment by accelerating the decrease in KB concentration and the restoration of a normal blood pH (which is lowered by KB). With the usual treatment, the decrease in KB concentration to acceptable low values (less than 1 mM) takes from 8 to 15 hr. Based on our animal experiments, we think that ketosis could be resolved in 1 or 2 hr by infusing pyruvate esters at a rate ranging from 50 to 120% of the caloric requirement of the patient. The latter is calculated from the body weight by the formula $$\text{Kcal/hr} = 4.6 \times (\text{body weight in kg})^{0.75}$$

Since the caloric density of DPAG and PADA is about 4 kcal/gram, the amount of pyruvate esters to be infused is about $$\text{Grams pyruvate ester/hr} = 0.9 \times (\text{body weight in kg})^{0.75}$$

Thus it is apparent that there has been provided, in accordance with the invention, a pyruvate composition that fully satisfies the objects, aims, and advantages set forth above. While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims.

We claim:

1. A method for treating dermatological illnesses or skin injury, or promoting skin health by aiding skin structure and function, said method comprising orally, intravenously or topically administering a therapeutically effective amount of a pyruvate compound in the form of a sugar-pyruvate ester, a polyol-pyruvate ester, pyruvate thioester, or a dihydroxyacetone-pyruvate ester.

2. The method of claim 1 wherein said pyruvate compound is dipyruvyl-acetyl-glycerol.

3. The method of claim 1 wherein said pyruvate compound is pyruvyl-acetyl-dihydroxyacetone.

4. The method of claim 1 wherein said pyruvate compound is pyruvyl-diacetyl-glycerol.

5. The method of claim 1 wherein said pyruvate compound is a pyruvate thioester of cysteine or homocysteine.

6. The method of claim 1 wherein said pyruvate thioester is a N-acetyl derivative thereof.

7. The method of claim 1 wherein said treating is directed to causations selected from the group consisting of radiation, cancer, photoaging, chemical, wind, cold, heat, autoimmune diseases, and inflammatory diseases.

8. The method of claim 1 wherein said pyruvate compound is glucose-pyruvate ester.

9. The method of claim 1 wherein said pyruvate compound is ribose-pyruvate ester.

10. A process for treating diabetic ketosis comprising administering an effective amount of a sugar-pyruvate ester a polyol-pyruvate ester, a pyruvate thioester, or a dihydroxyacetone-pyruvate ester.

11. The process of claim 10 wherein the pyruvate compound is dipyruvyl-acetyl-glycerol.

12. The process of claim 10 wherein said pyruvate compound is pyruvyl-acetyl-dihydroxyacetone.

13. The process of claim 10 wherein said pyruvate compound is pyruvyl-diacetyl-glycerol.

14. The process of claim 10 wherein said pyruvate compound is a pyruvate thioester of cysteine or homocysteine.

15. A method for treating a human in need of pyruvate with an effective dosage of a sugar-pyruvate ester or a polyol-pyruvate ester, by administering said sugar-pyruvate ester or polyol-pyruvate ester orally, intravenously or topically.

16. The method of claim 15 wherein said sugar is further comprised of 4 to 7 carbon atoms.

17. The method of claim 15 wherein said sugar is selected from the group consisting of ribose, glucose and fructose.

18. The method of claim 17 wherein said pyruvate derivative compound is of the formula:

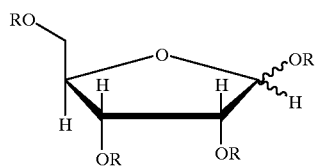

where R is H, pyruvyl, or a short-chain acyl, and with the proviso that at least one R group is pyruvyl.

19. The method of claim 17 wherein said pyruvate derivative compound is of the formula:

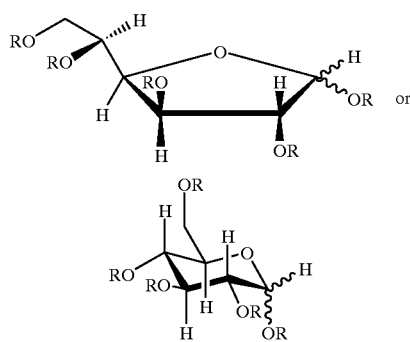

where R is H, pyruvyl, or a short-chain acyl, and with the proviso that at least one R group is pyruvyl.

20. The method of claim 13 wherein said polyol is selected from the group consisting of four to seven carbon polyols, aldosugars or ketosugars.

21. A topical formulation suitable for cosmetically or dermatologically administering to the skin, said formulation comprising a carrier and a compound selected from the group consisting of pyruvate thioester, dihydroxyacetone-pyruvate, a sugar-pyruvate ester or a polyol-pyruvate ester and mixtures thereof.

22. The topical formulation of claim 21 wherein said compound is of the formula:

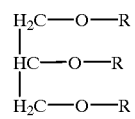

where zero, one or two R groups are H; one, two, or three R groups are pyruvyl and, one or two R groups may be a short-chain acyl selected from acetyl or propionyl.

23. The topical formulation of claim 21 wherein said compound is of the formula

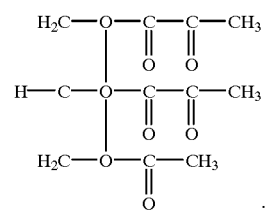

24. The topical formulation of claim 21 wherein said compound is of the formula:

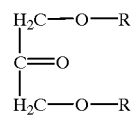

where zero or one R group is H, one or two R groups are pyruvyl and one R group may be a short-chain acyl selected from acetyl or propionyl.

25. The topical formulation of claim 21 wherein said compound is of the formula

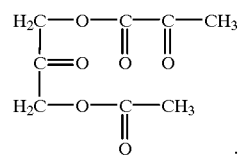

26. The topical formulation of claim 21, wherein said compound is of the formula

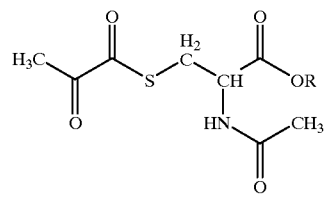

wherein R is selected from ethyl, methyl and alkyl groups.

27. The topical formulation of claim 21, wherein said compound is of the formula:

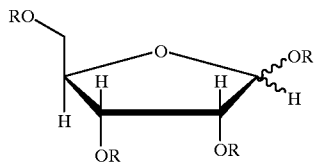

where R is H, pyruvyl, or a short-chain acyl, and with the proviso that at least one R group is pyruvyl.

28. The topical formulation of claim 21 wherein said pound is of the formula:

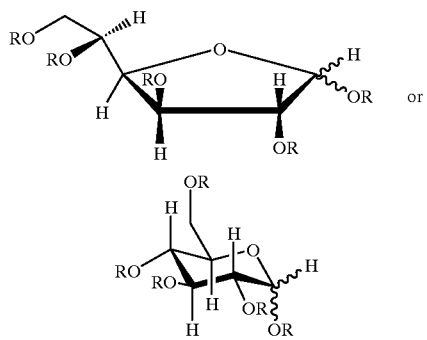

where R is H, pyruvyl, or a short-chain acyl, and with the proviso that at least one R group is pyruvyl.

29. The formulation of claim 21 having between 1 and 30 ppm pyruvate.

30. The formulation of claim 21 having at least 0.01% by weight pyruvate.

31. A compound for administering pyruvate to humans of the formula:

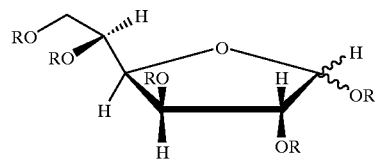

where R is H, pyruvyl, or a short-chain acyl, and
with the proviso that at least one R group is pyruvyl.

32. A compound for administering pyruvate to humans of the formula:

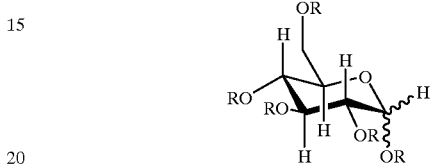

where R is H, pyruvyl, or a short-chain acyl, and
with the proviso that at least one R group is pyruvyl.

33. A compound for administering pyruvate to humans of the formula:

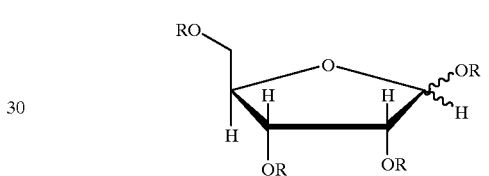

where R is H, pyruvyl, or a short-chain acyl, and
with the proviso that at least one R group is pyruvyl.

34. A method of stabilizing a cosmetic or dermatological composition comprising the addition of at least one esterified pyruvate.

* * * * *